US010420524B2

(12) United States Patent
Yamada

(10) Patent No.: US 10,420,524 B2
(45) Date of Patent: Sep. 24, 2019

(54) RADIOGRAPHING APPARATUS, CONTROL APPARATUS, CONTROL METHOD, AND STORAGE MEDIUM

(71) Applicant: CANON KABUSHIKI KAISHA, Tokyo (JP)

(72) Inventor: Daisuke Yamada, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 255 days.

(21) Appl. No.: 15/010,592

(22) Filed: Jan. 29, 2016

(65) Prior Publication Data

US 2016/0220214 A1 Aug. 4, 2016

(30) Foreign Application Priority Data

Jan. 30, 2015 (JP) ................................. 2015-017884

(51) Int. Cl.
*A61B 6/00* (2006.01)

(52) U.S. Cl.
CPC .......... *A61B 6/5258* (2013.01); *A61B 6/4266* (2013.01); *A61B 6/52* (2013.01); *A61B 6/5205* (2013.01); *A61B 6/5241* (2013.01); *A61B 6/5252* (2013.01); *A61B 6/54* (2013.01)

(58) Field of Classification Search
CPC ....... A61B 6/4266; A61B 6/52; A61B 6/5205; A61B 6/5241
USPC .................................................. 378/98.12, 62
See application file for complete search history.

(56) References Cited

U.S. PATENT DOCUMENTS

| | | | | |
|---|---|---|---|---|
| 5,123,056 A | * | 6/1992 | Wilson ................. | A61B 6/4476 348/E5.089 |
| 5,986,279 A | * | 11/1999 | Dewaele ............... | G01T 1/2012 250/363.01 |
| 6,078,699 A | * | 6/2000 | Lobregt ................. | A61B 6/481 348/E5.086 |
| 6,097,833 A | * | 8/2000 | Lobregt ................. | A61B 6/481 348/E5.089 |
| 6,215,848 B1 | * | 4/2001 | Linders ................. | A61B 6/481 250/370.09 |
| 6,269,177 B1 | * | 7/2001 | Dewaele ............... | A61B 6/4283 382/131 |
| 6,273,606 B1 | * | 8/2001 | Dewaele ............... | A61B 6/5241 378/174 |
| 6,459,094 B1 | * | 10/2002 | Wang ..................... | G03B 42/04 250/396 R |

(Continued)

FOREIGN PATENT DOCUMENTS

| CN | 1993984 A | 7/2007 |
|---|---|---|
| CN | 102821691 A | 12/2012 |

(Continued)

*Primary Examiner* — Allen C. Ho
(74) *Attorney, Agent, or Firm* — Canon U.S.A., Inc. IP Division

(57) ABSTRACT

A stitch imaging system, which uses a plurality of radiographic imaging units, includes an information acquisition unit configured to acquire information indicating a layout relationship among the plurality of radiographic imaging units, and a correction unit configured to correct a radiographic image or radiographic images acquired from at least one of the plurality of radiographic imaging units specified based on the information indicating the layout relationship, based on correction data specified based on the information indicating the layout relationship.

20 Claims, 15 Drawing Sheets

(56) References Cited

U.S. PATENT DOCUMENTS

| | | | | |
|---|---|---|---|---|
| 6,463,121 B1* | 10/2002 | Milnes | A61B 6/4482 | |
| | | | 378/62 | |
| 6,587,598 B1* | 7/2003 | Devillers | A61B 6/5241 | |
| | | | 382/130 | |
| 6,744,062 B2* | 6/2004 | Brahm | G03B 42/02 | |
| | | | 250/584 | |
| 6,748,049 B1 | 6/2004 | Yamamoto | | |
| 6,793,390 B2* | 9/2004 | Wang | G06T 3/0075 | |
| | | | 378/174 | |
| 6,895,076 B2* | 5/2005 | Halsmer | A61B 6/00 | |
| | | | 378/62 | |
| 6,895,106 B2* | 5/2005 | Wang | A61B 6/5241 | |
| | | | 382/132 | |
| 7,114,849 B2* | 10/2006 | Atzinger | A61B 6/08 | |
| | | | 378/206 | |
| 7,123,779 B2* | 10/2006 | Beuker | A61B 6/5241 | |
| | | | 382/294 | |
| 7,142,632 B2* | 11/2006 | Atzinger | A61B 6/4225 | |
| | | | 378/62 | |
| 7,247,858 B2* | 7/2007 | De Keyser | A61B 6/00 | |
| | | | 250/370.01 | |
| 7,265,355 B2* | 9/2007 | Chang | A61B 6/5241 | |
| | | | 250/370.09 | |
| 7,498,583 B2* | 3/2009 | Shoji | A61B 6/4266 | |
| | | | 250/370.09 | |
| 7,522,701 B2* | 4/2009 | Jensen | A61B 6/481 | |
| | | | 378/162 | |
| 7,555,100 B2* | 6/2009 | Wang | A61B 6/02 | |
| | | | 378/98.12 | |
| 7,558,438 B1 | 7/2009 | Sasada | | |
| 7,742,570 B2* | 6/2010 | Yamaguchi | A61B 6/5241 | |
| | | | 378/62 | |
| 7,881,434 B2* | 2/2011 | Akahori | A61B 6/4233 | |
| | | | 378/116 | |
| 7,978,816 B2* | 7/2011 | Matsuura | A61B 6/032 | |
| | | | 378/62 | |
| 8,064,572 B2* | 11/2011 | Sato | A61B 6/4429 | |
| | | | 378/206 | |
| 8,084,744 B2* | 12/2011 | Enomoto | A61B 6/4441 | |
| | | | 250/370.09 | |
| 8,199,880 B2* | 6/2012 | Yamada | A61B 6/00 | |
| | | | 378/114 | |
| 8,213,567 B2* | 7/2012 | Sakai | A61B 6/02 | |
| | | | 378/10 | |
| 8,213,572 B2* | 7/2012 | Minnigh | A61B 6/06 | |
| | | | 378/145 | |
| 8,344,327 B2* | 1/2013 | Yamaguchi | A61B 6/5241 | |
| | | | 250/363.07 | |
| 8,351,568 B2* | 1/2013 | Minnigh | A61B 6/4266 | |
| | | | 378/204 | |
| 8,360,639 B2* | 1/2013 | Kato | A61B 6/4233 | |
| | | | 378/197 | |
| 8,385,623 B2* | 2/2013 | Sakai | A61B 6/4476 | |
| | | | 378/62 | |
| 8,461,543 B2* | 6/2013 | Nishino | A61B 6/548 | |
| | | | 250/370.08 | |
| 8,550,709 B2* | 10/2013 | Nishino | A61B 6/04 | |
| | | | 378/145 | |
| 8,586,934 B2* | 11/2013 | Nakatsugawa | G01T 1/2985 | |
| | | | 250/363.02 | |
| 8,625,742 B2* | 1/2014 | Iwashita | A61B 6/4266 | |
| | | | 378/116 | |
| 8,748,834 B2* | 6/2014 | Enomoto | A61B 6/4233 | |
| | | | 250/370.08 | |
| 8,767,913 B2* | 7/2014 | Okuno | A61B 6/08 | |
| | | | 378/206 | |
| 8,792,616 B2* | 7/2014 | Tanaka | A61B 6/0457 | |
| | | | 378/20 | |
| 8,837,671 B2* | 9/2014 | Sakai | A61B 6/06 | |
| | | | 378/62 | |
| 8,899,832 B2* | 12/2014 | Fabrizio | A61B 6/08 | |
| | | | 378/195 | |
| 8,908,832 B2* | 12/2014 | Yamashita | A61B 6/06 | |
| | | | 378/62 | |
| 8,977,028 B2* | 3/2015 | Moon | A61B 6/461 | |
| | | | 382/131 | |
| 8,989,348 B2* | 3/2015 | Cox | G01N 23/04 | |
| | | | 378/146 | |
| 9,016,940 B2* | 4/2015 | Fabrizio | A61B 6/02 | |
| | | | 378/177 | |
| 9,050,023 B2* | 6/2015 | Okuno | A61B 6/08 | |
| 9,078,620 B2* | 7/2015 | Shin | A61B 6/4452 | |
| 9,121,809 B2* | 9/2015 | Cox | G01N 23/04 | |
| 9,149,247 B2* | 10/2015 | Lee | A61B 6/4452 | |
| 9,265,467 B2* | 2/2016 | Kamiya | A61B 6/5241 | |
| 9,541,509 B2* | 1/2017 | Akahori | A61B 6/486 | |
| 9,554,762 B2* | 1/2017 | Kim | A61B 6/48 | |
| 9,594,980 B1* | 3/2017 | Graham | H04N 5/23222 | |
| 9,626,589 B1* | 4/2017 | Graham | G06T 3/4038 | |
| 9,649,086 B2* | 5/2017 | Tajima | A61B 6/563 | |
| 9,697,923 B2* | 7/2017 | Tsuji | A61B 6/4266 | |
| 9,700,270 B2* | 7/2017 | Tateishi | A61B 6/4266 | |
| 9,700,277 B2* | 7/2017 | Okuno | A61B 6/06 | |
| 9,750,477 B2* | 9/2017 | Kitagawa | A61B 6/542 | |
| 9,801,596 B2* | 10/2017 | Tagawa | A61B 6/4233 | |
| 9,814,435 B2* | 11/2017 | Kim | A61B 6/469 | |
| 9,820,703 B2* | 11/2017 | Wojcik | A61B 6/4233 | |
| 9,861,329 B2* | 1/2018 | Shin | A61B 6/5205 | |
| 9,949,707 B2* | 4/2018 | Miyachi | A61B 6/5241 | |
| 10,058,294 B2* | 8/2018 | Tagawa | A61B 6/4266 | |
| 10,104,311 B2* | 10/2018 | Takekoshi | G06T 7/0012 | |
| 10,149,656 B2* | 12/2018 | Takagi | A61B 6/505 | |
| 2003/0048938 A1 | 3/2003 | Wang et al. | | |
| 2004/0071269 A1 | 4/2004 | Wang et al. | | |
| 2009/0304156 A1 | 12/2009 | Yamada | | |
| 2011/0057111 A1 | 3/2011 | Nishino | | |
| 2011/0233415 A1 | 9/2011 | Nakatsugawa et al. | | |
| 2011/0286582 A1 | 11/2011 | Iwashita et al. | | |
| 2012/0049080 A1 | 3/2012 | Enomoto | | |
| 2013/0077749 A1 | 3/2013 | Akahori et al. | | |
| 2013/0266118 A1 | 10/2013 | Senba | | |

FOREIGN PATENT DOCUMENTS

| | | |
|---|---|---|
| EP | 0867835 A2 | 9/1998 |
| EP | 1081947 A2 | 3/2001 |
| JP | 2000-278607 A | 10/2000 |
| JP | 2002-218202 A | 8/2002 |
| JP | 2005-257634 A | 9/2005 |
| JP | 2010-259688 A | 11/2010 |
| JP | 2011-004856 A | 1/2011 |
| JP | 2011-224338 A | 11/2011 |
| JP | 2011-224340 A | 11/2011 |
| JP | 2011-227047 A | 11/2011 |
| JP | 2012-045172 A | 3/2012 |
| JP | 2013-226243 A | 11/2013 |
| JP | 2015-165846 A | 9/2015 |

* cited by examiner

RADIOGRAPHING APPARATUS, CONTROL APPARATUS, CONTROL METHOD, AND STORAGE MEDIUM

BACKGROUND OF THE INVENTION

Field of the Invention

The present invention relates to a radiographing system using a plurality of radiographic imaging units.

Description of the Related Art

As one of image-capturing methods using a radiographic imaging unit, such as a film cassette, an imaging plate based on the Computed Radiography (CR) method, or a digital radiation detector, there is stitch imaging for capturing a larger subject than a region where a single radiographic imaging unit detects radiation.

Methods for implementing the stitch imaging include a method that lays out a plurality of radiographic imaging units and irradiates the subject with a single shot of radiation, besides a method that irradiates the subject with a plurality of shots of radiation while moving a single radiographic imaging unit. A plurality of radiographic images acquired by any of these methods is appropriately arranged and stitched, by which an image of the larger subject than the region where the single radiographic imaging unit detects radiation can be acquired.

In a stitch imaging system using the plurality of radiographic imaging units, in a case where the radiographic imaging units are laid out in such a manner that some regions overlap each other in the radiographic images that can be acquired from this plurality of radiographic imaging units, the radiographic image from one radiographic imaging unit relating to this overlap region may contain a structure of another radiographic imaging unit appearing therein. This appearance necessitates employment of a different correction for the radiographic image with the structure appearing therein from a correction employed for the radiographic image without the structure appearing therein.

SUMMARY OF THE INVENTION

According to an aspect of the present invention, a stitch imaging system, which uses a plurality of radiographic imaging units, includes an information acquisition unit configured to acquire information indicating a layout relationship among the plurality of radiographic imaging units, and a correction unit configured to correct a radiographic image or radiographic images acquired from at least one of the plurality of radiographic imaging units specified based on the information indicating the layout relationship, based on correction data specified based on the information indicating the layout relationship.

Further features of the present invention will become apparent from the following description of exemplary embodiments with reference to the attached drawings.

DESCRIPTION OF THE EMBODIMENTS

Figure 1:
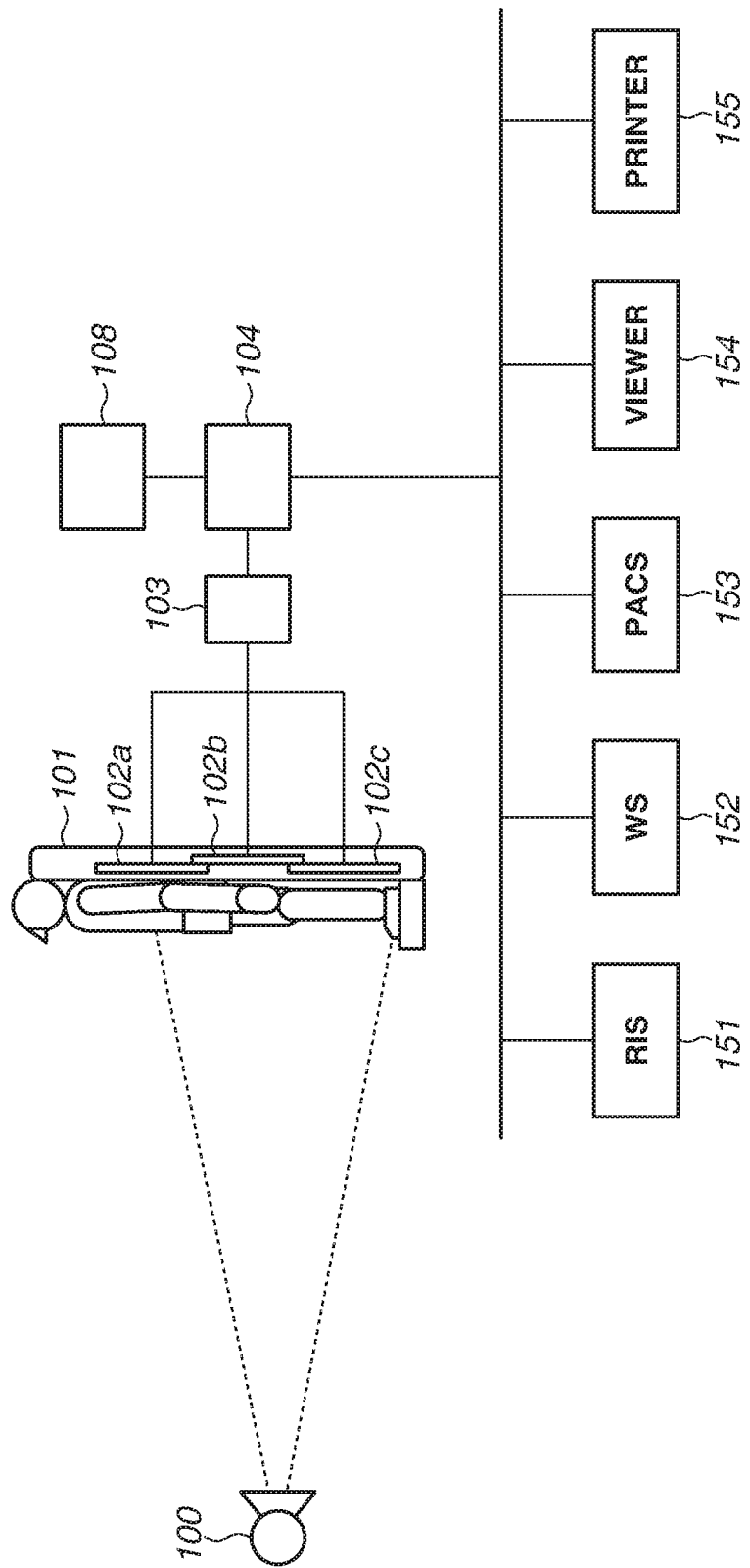
FIG. 1 is a block diagram illustrating a configuration of an information system including a radiographing system according to an exemplary embodiment.

A radiographing system according to an exemplary embodiment will be described with reference to FIG. 1. FIG. 1 illustrates a configuration of an information system including a stitch imaging system using an X-ray as radiation, which is an example of the radiographing system. This information system includes, for example, the radiographing system, a radiology information system (RIS) 151, a workstation (WS) 152, a picture archiving and communication system (PACS) 153, a viewer 154, and a printer 155. The RIS 151 is a system that manages an order for radiographic imaging, and transmits the order for radiographic imaging to the radiographing system. The WS 152 is an image processing terminal, and processes a radiographic image captured by the radiographing system to acquire an image for use in diagnosis. The PACS 153 is a database system that contains medical images provided from the radiographing system and another modality (a medical imaging system or a medial image-capturing apparatus). The PACS 153 includes a storage unit that stores the medical images and appendant information, such as image-capturing conditions applied for these medical images, and a controller that manages the information stored in this storage unit. The viewer 154 is a terminal for use in image diagnosis, and reads out the image stored in the PACS 153 or the like to display this image for the diagnosis. The printer 155 is, for example, a film printer, and outputs the image stored in the PACS 153 onto a film.

The stitch imaging system, which is an example of the radiographing system, includes a radiation generation unit 100, a platform 101, a plurality of radiographic imaging units 102a, 102b, and 102c (or a cassette A, a cassette B, and a cassette C), a relay 103, a control apparatus 104, and a touch panel monitor 108 that serves as both a display unit and an operation unit. These components are connected to one another via a cable. The radiation generation unit 100 emits the radiation to the plurality of radiographic imaging units 102a, 102b, and 102c simultaneously for irradiation. When the radiation is emitted to the plurality of radiographic imaging units 102a, 102b, and 102c for the irradiation, the plurality of radiographic imaging units 102a, 102b, and 102c acquires radiographic images, and this plurality of radiographic images is transmitted to the control apparatus 104 via the relay 103.

The control apparatus 104 is, for example, an electronic computer (a personal computer (PC)) with a desired software program installed therein, and generates a stitched image by performing image processing including stitching processing on this plurality of radiographic images. Further, the control apparatus 104 causes this stitched image to be displayed on the touch panel monitor 108. In this manner, the stitch imaging system carries out the stitch imaging of emitting the radiation to the plurality of radiographic imaging units 102a, 102b, and 102c simultaneously for the irradiation. Further, the control apparatus 104 generates a Digital Imaging and Communications in Medicine (DICOM) image based on this stitched image and appendant information, such as an image-capturing condition applied for this stitched image. Then, the control apparatus 104 transmits this DICOM image to the WS 152 or the PACS 153.

An image-capturing order for the stitch imaging is, for example, transmitted from the RIS 151 to the control apparatus 104. In this case, the control apparatus 104 receives, from the RIS 151, an image-capturing information identification (ID) indicating the stitch imaging, and information indicating an image-capturing site that should be captured by the stitch imaging, such as an entire lower limb and an entire spine, and reads out an image-capturing condition corresponding to this received information from a storage unit of the control apparatus 104. Alternatively, the control apparatus 104 may be assumed to acquire image-capturing information including information indicating the image-capturing site, an image-capturing method, and the image-capturing condition from an operation input via the touch panel monitor 108.

Besides the touch panel monitor 108, an operation unit such as a mouse and a keyboard may be connected to the control apparatus 104.

As illustrated in FIG. 1, the radiographic imaging units 102a, 102b, and 102c are laid out in such a manner that a region that the radiographic imaging unit 102a captures and a region that the radiographic imaging unit 102b captures partially overlap each other so as to establish a continuous imaging region. This layout results in the appearance of a predetermined structure in the radiographic image acquired by the radiographic imaging unit 102b. On the platform 101 according to the present exemplary embodiment, only a radiographic imaging unit 102 disposed in the middle among the radiographic imaging units 102a, 102b, and 102c disposed in the order is located at a position farther away from the radiation generation unit 100 than the other radiographic imaging units 102, and is arranged in such a manner that the imaging region thereof partially overlaps the imaging regions of the other radiographic imaging units 102. Laying out the radiographic imaging units 102a, 102b, and 102c in this manner can reduce the number of radiographic images with the structure appearing therein.

The radiographic image with the structure appearing therein is corrected by, for example, the control apparatus 104 or the radiographic imaging unit 102 with use of correction data for correcting the structure that is separately acquired, so that the number of structures appearing in the radiographic image(s) is reduced.

Figure 2:
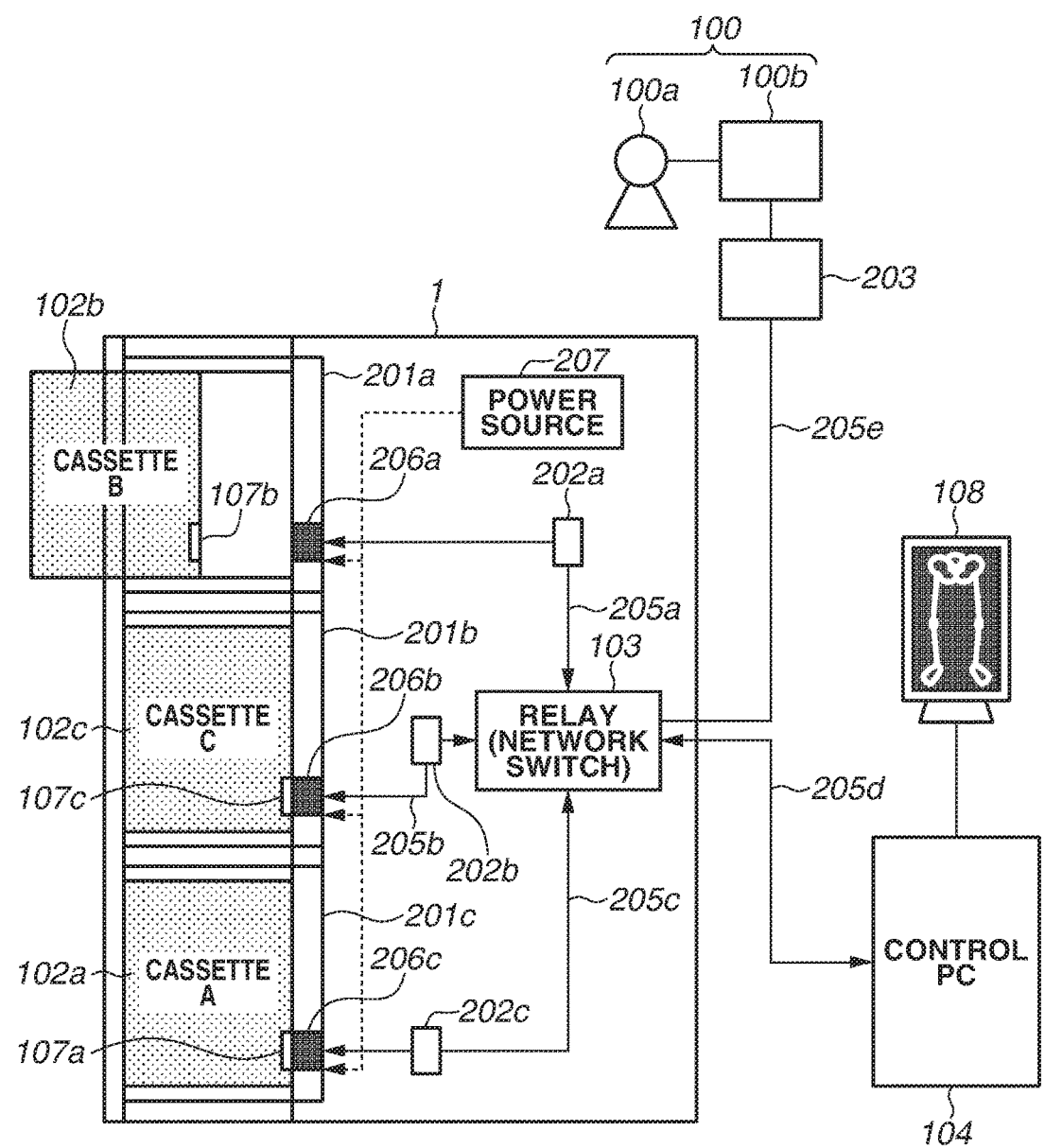
FIG. 2 is a block diagram illustrating a configuration of a stitch imaging system according to the exemplary embodiment.

A configuration of the stitch imaging system according to the present exemplary embodiment will be described in detail with reference to FIG. 2. The radiation generation unit 100 includes a radiation irradiation unit 100a that includes a diaphragm for setting a range to be irradiated with the radiation and a radiation source for generating the radiation, and a generation control unit 100b for controlling the irradiation with the radiation by the radiation irradiation unit 100a. An irradiation switch is further connected to the generation control unit 100b to input a signal for instructing the generation control unit 100b about a timing of starting the irradiation to the generation control unit 100b. The radiation generation unit 100 may further include an interface unit 203 that communicates with the radiographic imaging units 102a, 102b, and 102c. In this case, the radiation generation unit 100 and the platform 101 are connected communicably with each other via a network cable 205e, such as an Ethernet (registered trademark) cable. The control apparatus 104 is connected to the platform 101 communicably with each other via a network cable 205d.

The platform 101 is a holder unit that fixes the plurality of radiographic imaging units 102a, 102b, and 102c for carrying out the stitch imaging. In one exemplary embodiment, the platform 101 has three positions for fixing the radiographic imaging units 102a, 102b, and 102c, and includes a housing portion 201 that houses the radiographic imaging unit 102, and a platform connector 206 at each of the fixation positions. The position of each of the connectors 206 is determined in such a manner that the platform connector 206 and a radiographic imaging unit connector 107 are fitted to each other when the radiographic imaging unit 102 is fixed in the housing portion 201.

The platform 101 includes housing portions 201a, 201b, and 201c that house the radiographic imaging units 102a, 102b, and 102c, respectively, platform connectors 206a, 206b, and 206c respectively disposed along sidewalls of the housing portions 201a, 201b, and 201c and respectively provided for establishing wired connections with the radiographic imaging units 102a, 102b, and 102c, and the relay 103 (a network switch).

The platform connectors 206a, 206b, and 206c are connected to the relay 103 via network cables 205a, 205b, and 205c, respectively. Further, the platform connectors 206a, 206b, and 206c are connected to the radiographic imaging unit connectors 107 of the radiographic imaging units 102a, 102b, and 102c, respectively. In the example illustrated in FIG. 2, a radiographic imaging unit connector 107b of the radiographic imaging unit 102b, a radiographic imaging unit connector 107c of the radiographic imaging unit 102c, and a radiographic imaging unit connector 107a of the radiographic imaging unit 102a are connected to the platform connector 206a, the platform connector 206b, and the platform connector 206c, respectively.

The relay 103 is the network switch, and one of a plurality of physical ports thereof is extended out of the platform 101 so as to be connectable to the control apparatus 104. This port is fixedly wired so as to be connected to a communication port of the control apparatus 104, when the platform 101 and the control apparatus 104 are set up in a user's use environment. The remaining ports are wired so as to be connected to the platform connectors 206a, 206b, and 206c at the cassette fixation positions. This wiring is fixedly wired when the platform 101 is manufactured, so that corresponding relationships between the platform connectors 206a, 206b, and 206c and the physical ports of the relay 103 do not change over the course of the user's use.

The platform 101 may further include a power source 207 that supplies power to the radiographic imaging units 102a, 102b, and 102c. This configuration leads to connections of two cable systems, a network cable and a power source cable to each of the platform connectors 206a, 206b, and 206c. Instead of the power source 207, power source units 202a, 202b, and 202c may be provided with respect to the housing portions 201a, 201b, and 201c, respectively. This configuration leads to connections of two systems, a communication cable and a power source cable between the platform connector 206 and the power source unit 202, and a connection of a communication cable between the power source unit 202 and the relay 103.

The radiographic images provided from the radiographic imaging units 102a, 102b, and 102c are transmitted to the control apparatus 104 via the radiographic imaging unit connectors 107a, 107b, and 107c, the platform connectors 206a, 206b, and 206c, and the relay 103.

In another exemplary embodiment, the platform 101 may be configured to include a radiographic imaging unit connection unit and a platform connection unit that perform near field wireless communication, such as TransferJet, instead of the radiographic imaging unit connector 107 and the platform connector 206. Alternatively, the radiographic imaging unit 102 may be configured to wirelessly communicate with the relay 103 directly without communicating via the platform connector 206 and the like. This configuration leads to the radiographic imaging unit 102 wirelessly communicating with the platform 101 and the relay 103, and makes the communication path partially wireless between the radiographic imaging unit 102 and the control apparatus 104.

The relay 103 is disposed inside the platform 101, but is not limited thereto and may be disposed outside the platform 101. Further, the relay 103 and the radiation generation unit 100 may be connected to each other via a wireless communication path, and the relay 103 and the control apparatus 104 may be connected to each other via a wireless communication path.

To carry out the stitch imaging, first, the radiographic imaging units 102a, 102b, and 102c are fixedly mounted onto the respective fixation positions of the platform 101 provided for the stitch imaging. By this mounting, the platform connectors 206a, 206b, and 206c and the radiographic imaging unit connectors 107a, 107b, and 107c are fitted to each other, respectively. By this fitting, respective main control circuits inside the individual radiographic imaging units 102a, 102b, and 102c are connected to the relay 103 via the radiographic imaging unit connectors 107a, 107b, and 107c, the platform connectors 206a, 206b, and 206c, and the network cables 205a, 205b, and 205c, respectively. As a result, a network including the individual radiographic imaging units 102a, 102b, and 102c and the control apparatus 104 is created. The radiographic imaging units 102a, 102b, and 102c and the relay 103 are connected in an individually attachable and detachable manner by the fitted attachment between the radiographic imaging unit connectors 107a, 107b, and 107c and the platform connectors 206a, 206b, and 206c.

The creation of the network allows each of the cassettes A, B, and C and the control apparatus 104 to communicate with each other, thereby causing the software of the control apparatus 104 to start control communication with each of the cassettes A, B, and C. This control communication allows the software of the control apparatus 104 to recognize that each of the radiographic imaging units 102a, 102b, and 102c is mounted on the platform 101, and also recognize a position where each of the cassettes A, B, and C is mounted on the holder. How the position recognition proceeds will be described below.

When the user completes the operation of mounting the radiographic imaging units 102a, 102b, and 102c, and the software can confirm that the radiographic imaging units 102a, 102b, and 102c are mounted normally, the software displays the completion of the preparation on the touch panel monitor 108 connected to the control apparatus 104. The user confirms the display indicating the completion of the preparation, and carries out the image-capturing. As illustrated in FIG. 1, the image-capturing is carried out in such a manner that a subject is positioned in front of the platform 101, and the subject in a wide range extending across the plurality of radiographic imaging units 102a, 102b, and 102c can be imaged by being irradiated with the radiation a single time.

After the image-capturing is carried out, a main control circuit 150 of each of the cassettes A, B, and C generates image data by scanning a two-dimensional image sensor 120. The generated image data is transferred to the control apparatus 104. In this case, the image data may be transferred with use of a communication path via a wired communication circuit 180 and the radiographic imaging unit connector 107 built in the radiographic imaging unit 102, the platform connector 206, and the like. Alternatively, the image data may be transferred via a wireless communication circuit 160 built in the radiographic imaging unit 102, and a not-illustrated wireless access point connected to the control apparatus 104.

The control apparatus 104 performs image processing for rearranging the images received from the individual radiographic imaging units 102a, 102b, and 102c by referring to recognized information about the positions where the cassettes A, B, and C are mounted, and connectively combines them. The combined image is presented to the user as a stitch imaging image that contains information of the subject in the wide range.

Figure 3:
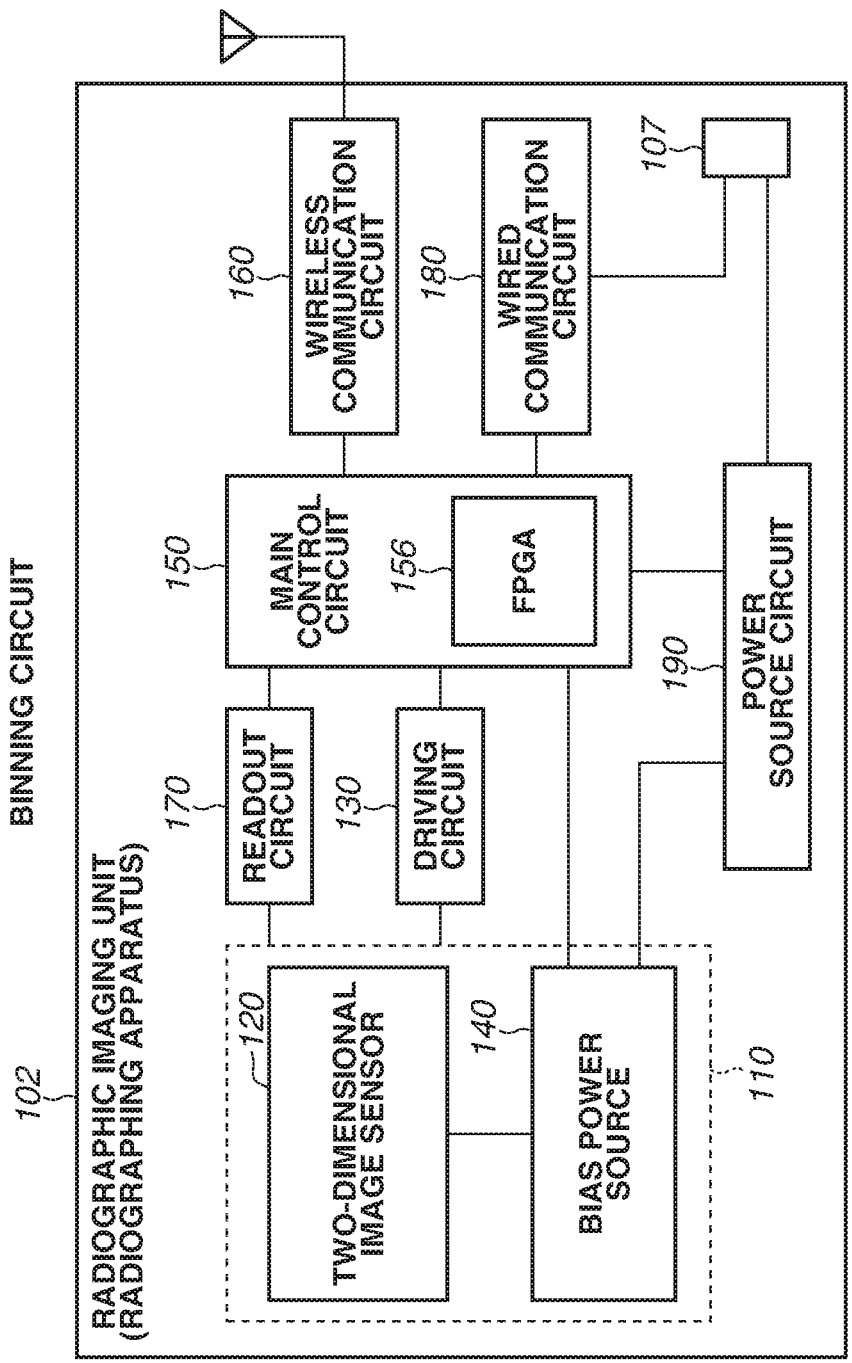
FIG. 3 is a block diagram illustrating a configuration of a radiographic imaging unit according to the exemplary embodiment.

A configuration of the radiographic imaging unit (a radiographing apparatus) 102 according to the present exemplary embodiment will be described with reference to FIG. 3. The radiographic imaging unit 102 includes a radiation sensor 110, a driving circuit 130, a readout circuit 170, the main control circuit 150, the wireless communication circuit 160, the wired communication circuit 180, the radiographic imaging unit connector 107, and a power source circuit 190. The radiation sensor 110 includes the two-dimensional image sensor 120. The two-dimensional image sensor 120 includes a pixel array in which a plurality of pixels is arrayed in the form of a matrix, a row selection line that is commonly connected to pixels lined up in a row direction and transmits a driving signal issued from the driving circuit 130, and a column signal line that is commonly connected to pixels lined up in a column direction and transmits an image signal to the readout circuit 170. A bias power source 140 is connected to each of the pixels of the two-dimensional image sensor 120. The pixels each include a photoelectric conversion element having one end connected to the bias power source 140, and a switching element connected to another end of this photoelectric conversion element. A base electrode of the switching element is connected to the row selection line, and the photoelectric conversion element and the column signal line are connected to a collector and an emitter of the switching element. The two-dimensional image sensor 120 generates the image based on a distribution of intensity of the radiation incident on this image sensor 120.

Other than those, the radiation sensor 110 may include a binning circuit that includes a switching element for connecting a plurality of pixels to one another, and combines image signals. For example, the switching element is connected to four pixels, vertically adjacent two pixels and horizontally adjacent two pixels. This configuration allows the radiation sensor 110 to combine the image signals before the image signals are digitized.

The driving circuit 130 controls an on state and an off state of the switching element by outputting the driving signal. When the switching element is controlled into the off state, this causes the image signal to be stored into a parasitic capacitance or the like of the photoelectric conversion element. When the switching element is controlled into the on state, this causes the stored image signal to be output via the column signal line. The readout circuit 170 includes an amplifier for amplifying the image signal output from the radiation sensor 110, and an analog-to-digital (A/D) converter for converting the image signal into a digital signal. The image signal is read out as the digital signal by them.

The driving circuit 130 performs control of collectively applying off-state voltages and control of sequentially applying on-state voltages to the row selection lines corresponding to the individual rows of the pixel array. The off-state voltages cause the radiation sensor 110 to transition to a storage state. The control of sequentially applying the on-state voltages causes the signals of the pixel array to be sequentially output to the readout circuit 170. By theses control procedures, the radiographic imaging unit 102 performs an operation of initializing the pixel array before causing the radiation sensor 110 to transition to the storage state, and an operation of reading out the image signals acquired from the storage.

The driving circuit 130 may conduct interlace driving of sequentially applying the on-state voltages to 2n rows, i.e., even-numbered rows, and then sequentially applying the on-state voltages to 2n−1 rows, i.e., odd-numbered rows after that. By this driving, the driving circuit 130 realizes reading out the image signals while thinning out the image signals. The thinning-out driving is not limited to the method that conducts this driving at intervals of one row as described above, and may be set to be conducted at intervals of two rows or m−1 rows. A desired value is adopted as a rate at which the image signals are thinned out in this manner. The driving circuit 130 may be set to sequentially apply the on-state voltages, like sequentially applying the on-state voltages to an mn row, an mn+1 row, an mn+2 row, . . . and an mn+(m−1) row, when m−1 is set as the rate at which the image signals are thinned out.

Alternatively, the driving circuit 130 can also conduct partial readout of the image signals, which means outputting image signals acquired from pixels around a center of the pixel array prior to the other image signals. In this case, supposing that the pixel array is constituted by M rows and N columns, M/2×N/2 image signals of an M/4+1 row to a 3M/4 row and an N/4+1 column to a 3N/4 column are output. The above-described operations performed by the driving circuit 130 are performed according to control from the main control circuit 150.

The main control circuit 150 integrally controls the radiographic imaging unit 102. Further, the main control circuit 150 includes a processing circuit implemented by a field-programmable gate array (FPGA) 156, and generates the radiographic image and performs the image processing thereby. The FPGA 156 can perform processing for acquiring an image small in data amount by, for example, the binning processing that sums up values of the adjacent 2×2 pixels, the thinning-out processing that partially thins out the pixels and partially extracts the pixels, or processing that extracts a continuous region, when acquiring the digital radiographic image.

Further, examples of the image processing that may be performed by the FPGA 156 include a dark correction for reducing a dark current component in the radiographic image, a gain correction for correcting a variation in an input/output characteristic of the pixel, a correction of a defective pixel, and processing for reducing a noise, such as a line noise.

The wireless communication circuit 160 and the wired communication circuit 180 can transmit and receive a control command and data, such as a signal from the control apparatus 104 and the radiation generation unit 100. Further, the wireless communication circuit 160 transmits a signal indicating a state of the radiographic imaging unit 102, and the radiographic image. The wireless communication circuit 160 includes an antenna, and performs wireless communication mainly when the wired cable 205 is not connected to the radiographic imaging unit connector 107. The radiographic imaging unit connector 107 is connected to the wired communication circuit 180, and the wired communication circuit 180 controls the wired communication. The connector 107 is provided for the communication and the power supply, and the communicated information and the power are transmitted to the wired communication circuit 180 and the power source circuit 190, respectively. The power source circuit 190 includes a battery, and produces a voltage required for the operation of the radiographic imaging unit 102 to supply the voltage to each of the units. The main control circuit 150 specifies which communication method should be used, the wireless communication or the wired communication. For example, the wired communication is specified if the wired cable 205 is connected to the connector 107, and the wireless communication is specified if the wired cable 205 is not connected but a connection via the wireless communication is established. Neither communication method is specified if the wired cable 205 is not connected and a connection via the wireless connection is also not established. In this case, for example, the radiographic image is not transmitted, and is stored into a nonvolatile memory connected to the main control circuit 150.

If transmitting the radiographic image with any of the communication methods specified, the main control circuit 150 transfers a preview image smaller in data amount than the radiographic image acquired by the radiation sensor 110 prior to this radiographic image. Then, the main control circuit 150 transmits an image that contains data uncontained in the preview image after completion of the transmission of this preview image.

This transmission allows the control apparatus 104 side to quickly check whether the image-capturing has been appropriate. The preview image and the image that contains the data uncontained in the preview image may be transmitted according to the readout of the image signals by the readout circuit 170 and the generation of the preview image by the main control circuit 150. Alternatively, the main control circuit 150 may be set to transmit these images according to a signal from the control apparatus 104. In this manner, the control apparatus 104 controls the communication with the plurality of radiographic imaging units 102a, 102b, and 102c, which can reduce an influence due to simultaneous transmission of large-volume data from the plurality of radiographic imaging units 102a, 102b, and 102c, thereby realizing efficient image communication.

Because this influence on the communication can be less likely to arise in some cases, for example, when the radiographic imaging unit 102 is connected to the control apparatus 104 via the wired communication or the communication capacity is sufficiently large, the main control circuit 150 may be configured to change the method for transmitting the images according to the communication method between the control apparatus 104 and the radiographic imaging unit 102.

One of states of the radiographic imaging unit 102 is a first state in which power is supplied only to the wireless communication circuit 160 and the wired communication circuit 180, and no power is supplied from the bias power source 140 to the two-dimensional image sensor 120 (a so-called sleep state). Further, another state of the radiographic imaging unit 102 is a second state in which power is supplied from the bias power source 140 to the two-dimensional image sensor 120. In the second state, the initialization operation is conclusively performed, and the radiographic imaging unit 102 is ready to generate the image by transitioning to the storage state in response to an instruction from outside. The radiographic imaging unit 102 transmits the signal indicating the above-described state according to a request signal from outside.

In a case where the radiation generation unit 100 is provided with the interface unit 203, synchronized communication is performed between the radiation generation unit 100 and the radiographic imaging unit 102. In response to pressing of the irradiation switch, the interface unit 203 transmits a first signal to each of the radiographic imaging units 102a, 102b, and 102c. According to this first signal, the driving circuit 130 of each of the radiographic imaging units 102a, 102b, and 102c causes the two-dimensional image sensor 120 to perform the initialization operation, and to transition to the storage state. Upon completion of the initialization and the transition to the storage state, each of the radiographic imaging units 102a, 102b, and 102c transmits a second signal to the interface unit 203. The interface unit 203 determines whether the second signals are received from all of radiographic imaging units 102 to be used for a certain stitch imaging, and inputs a signal for permitting the irradiation to the generation control unit 100b if the interface unit 203 has determined that the second signals are received from all of them. According thereto, the radiation is emitted from the radiation irradiation unit 100a for the irradiation. Controlling the units in this manner can prevent the radiation irradiation from being carried out before the radiographic imaging units 102a, 102b, and 102c transition to the storage state, thereby reducing unnecessary exposure.

In a case where the radiation generation unit 100 is not provided with the interface unit 203, the radiation generation unit 100 irradiates the subject with the radiation in response to the pressing of the irradiation switch. Each of the radiographic imaging units 102a, 102b, and 102c detects this start of the radiation irradiation, and transitions to the storage state. The radiographic imaging unit 102a, 102b, and 102c may each detect the start of the irradiation based on a signal acquired by the two-dimensional image sensor 120, or may detect the start of the irradiation by a sensor for detecting the start of the irradiation that is provided separately from the radiation sensor 110.

The main control circuit 150 specifies which mode should be employed, a first image-capturing mode of performing the synchronized communication or a second image-capturing mode of detecting the radiation, according to a signal input from outside.

Figure 4:
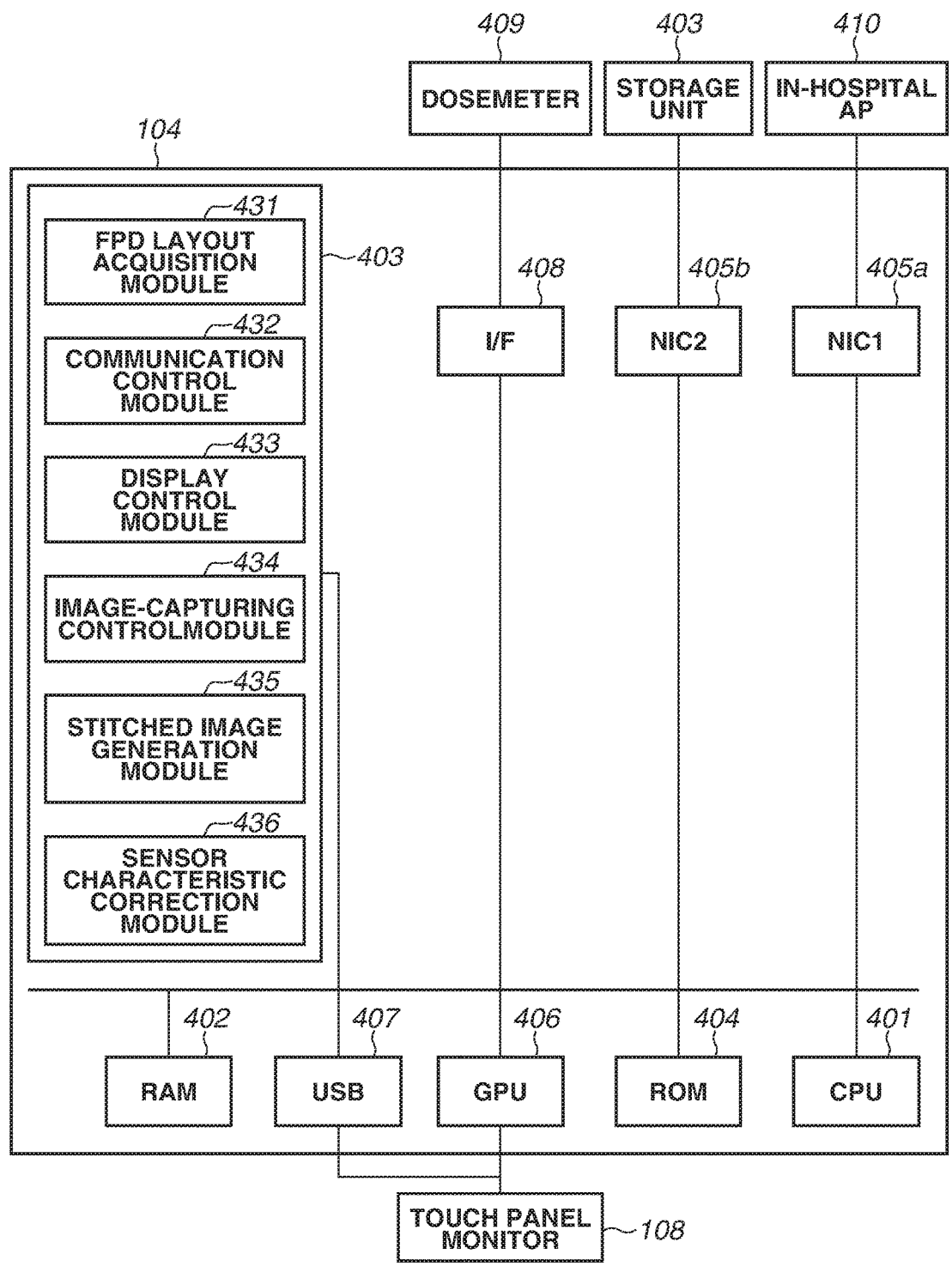
FIG. 4 is a block diagram illustrating a configuration of a control apparatus according to the exemplary embodiment.

A configuration of the control apparatus 104 according to the present exemplary embodiment will be described with reference to FIG. 4. The control apparatus 104 includes a central processing unit (CPU) 401, a random access memory (RAM) 402, a storage unit 403, a read only memory (ROM) 404, network interface cards (NICs) 405 (405a and 405b), a graphic processing unit (GPU) 406, a universal serial bus (USB) interface 407, and a communication interface (I/F) 408. These components are communicably connected to one another via an internal bus. The CPU 401 is a control circuit that comprehensively controls the control apparatus 104 and each of units connected to the control apparatus 104, and may include a plurality of CPUs. The RAM 402 is a memory used for loading a program for performing, for example, processing illustrated in FIG. 6 that will be described below, and various kinds of parameters, which are stored in the storage unit 403 or the like. The CPU 401 sequentially executes commands contained in the program loaded into this RAM 402, by which the processing according to the present exemplary embodiment is realized. The storage unit 403 is a memory such as a hard disk drive (HDD) and a solid state drive (SSD), and stores the above-described program, the radiographic image such as the stitched image acquired by the image-capturing, the image-capturing order, the image-capturing information, and in addition thereto, the various kinds of parameters. The NICs 405 are an example of a communication unit that communicates with an external apparatus. The control apparatus 104 according to the present exemplary embodiment includes a first NIC 405a and a second NIC 405b. The first NIC 405a is connected to an in-hospital access point (AP) 410 for connecting to an in-hospital network, and the second NIC 405b is connected to the relay 103 that relays the communication of the radiographing system. The GPU 406 is an image processing unit, and performs the image processing according to control from the CPU 401. An image acquired as a result of the image processing is output and displayed onto the touch panel monitor 108. The USB I/F 407 is a communication unit that acquires information relating to an operation input from the touch panel monitor 108, and is interpreted as the operation input by the CPU 401. The communication I/F 408 is, for example, a communication unit supporting a standard such as Recommended Standard 232 version C (RS232C), Ethernet (registered trademark), and USB, and communicates with a dosemeter (a dose measurement device) 409 to receive information indicating a radiation dose.

The program stored in the storage unit 403 includes, for example, a flat panel detector (FPD) (radiographic imaging unit) layout acquisition module 431, a communication control module 432, a display control module 433, an image-capturing control module 434, a stitched image generation module 435, and a correction module 436.

The FPD layout acquisition module 431 acquires information indicating a layout relationship among the plurality of radiographic imaging units 102a, 102b, and 102c to be used to carry out the one stitch imaging. The information indicating the layout relationship is, for example, information indicating that the radiographic imaging units 102a, 102b, and 102c are laid out so as to be arranged in this order, or information indicating that the radiographic imaging unit 102b is located in the middle of them. The information indicating the layout relationship may contain information indicating rotational states of the radiographic imaging units 102a, 102b, and 102c. Such information indicating the layout relationship is acquired by the CPU 401 based on, for example, information, received by the second NIC 405b, indicating the communication paths of the radiographic imaging units 102a, 102b, and 102c, and correspondence information, stored in the storage unit 403, indicating correspondence relationships between the communication paths and the layout positions. For example, in a case where the platform connectors 206a, 206b, and 206c are disposed fixedly relative to the housing portions 201a, 201b, and 201c as illustrated in FIG. 2, the layout positions of the plurality of radiographic imaging units 102a, 102b, and 102c can be identified by referring to the information indicating the communication paths. For example, in a case where the relay 103 is a layer 2 network switch, the relay 103 performs an operation of learning relationships between the physical ports and media access control (MAC) addresses, and correspondence relationships between the radiographic imaging units 102a, 102b, and 102c and the physical ports are acquired as the information indicating the communication paths with use of this operation.

This information indicating the layout relationships acquired in this manner is stored into the storage unit 403. Alternatively, the second NIC 405b may receive the information indicating the layout relationship. In this case, the relay 103 or the platform 101 is assumed to have a function of acquiring the information indicating the layout relationship based on the information indicating the communication paths and the like.

The information indicating the layout relationship is, for example, referred to during the course of execution of the stitched image generation module 435, and used in the processing for stitching the plurality of radiographic images. The information indicating the layout relationship in this case is information for identifying which radiographic images contain an overlap region therebetween. Further, the information indicating the layout relationship is, for example, referred to by the CPU 401 to determine which radiographic image should be subjected to execution of the correction processing for removing the structure appearing therein during the course of execution of the correction module 436. The information indicating the layout relationship in this case is information for identifying which one of the radiographic imaging units 102a, 102b, and 102c has output the image with the structure appearing therein, and corresponds to information for identifying which one of the radiographic imaging units 102a, 102b, and 102c radiographic imaging unit is located in the middle of the radiographic imaging units 102a, 102b, and 102c in the imaging system illustrated in FIG. 1.

The communication control module 432 controls the communication by the first NIC 405a and the second NIC 405b. Execution of the communication control module 432 causes, for example, the control apparatus 104 to transmit the signals for causing the states of the plurality of radiographic imaging units 102a, 102b, and 102c to transition to the second state to the radiographic imaging units 102a, 102b, and 102c according to an operation input from the touch panel monitor 108 or the like. This operation input is carried out, for example, according to an operation input for selecting one of a plurality of image-capturing conditions contained in the image-capturing order and then the CPU 401 specifying this image-capturing condition based thereon. In response to this operation input, the second NIC 405b transmits the signals for causing the states to transition, to the radiographic imaging units 102a, 102b, and 102c. Then, the second NIC 405b will receive response signals thereto.

Further, the execution of the communication control module 432 causes, for example, the control apparatus 104 to receive the radiographic image from each of the plurality of radiographic imaging units 102a, 102b, and 102c. At this time, the control apparatus 104 is assumed to first receive the preview image (a first image) small in data amount and then receive the image that contains the remaining data (a second image) after that, from each of the plurality of radiographic imaging units 102a, 102b, and 102c. In this case, the control apparatus 104 is assumed to, when receiving the preview image (the first image) from one radiographic imaging unit 102, restrict the reception of the first or second image from the other radiographic imaging units 102. Therefore, each of the radiographic imaging units 102a, 102b, and 102c is assumed to be set to transmit the image according to an instruction from the control apparatus 104, and the control apparatus 104 is assumed to instruct one radiographic imaging unit 102 to transmit the second image according to, for example, completion of the reception of the preview images (the first images) from all of the radiographic imaging units 102a, 102b, and 102c. By this control, the large-volume data is prevented from being transmitted from the plurality of radiographic imaging units 102a, 102b, and 102c to the relay 103 simultaneously, thereby improving efficiency of the communication.

The radiographic imaging unit side can also perform a transmission method in which the radiographic image is transmitted in response to the readout of the image signals (a first transmission method), besides the transmission method in which the image is transmitted in response to the instruction signal as described above (a second transmission method). The transmission method to be performed is, for example, specified according to a signal from the control apparatus 104. For example, the first transmission method is specified in the case where the radiographic imaging unit 102 performs the wireless communication, and the second transmission method is specified in the case where the radiographic imaging unit 102 performs the wired communication. In the case where the transmission method is specified according to the communication configuration in this manner, the radiographic imaging unit 102 can specify the transmission method regardless of the signal from outside.

Besides that, by executing the communication control module 432, the CPU 401 cause a DICOM image file containing the radiographic image acquired by the radiographic imaging or the stitch imaging to be transmitted to the PACS 153 via the first NIC 405a.

In one exemplary embodiment, the FPGA 156 of the radiographic imaging unit 102 performs the processing for correcting the structure appearing in the radiographic image. In this case, the CPU 401 specifies the radiographic imaging unit 102 to be instructed to perform the processing for correcting the structure among the plurality of radiographic imaging units 102a, 102b, and 102c during the course of the execution of the communication control module 432. As an example thereof, the radiographic imaging unit 102b located in the middle of the radiographic imaging units 102a, 102b, and 102c illustrated in FIG. 1 is specified with use of the information indicating the layout relationship. Then, the CPU 401 causes the second NIC 405b to transmit an instruction signal for instructing the radiographic imaging unit 102b to perform the processing for correcting the structure to the radiographic imaging unit 102b.

The display control module 433 is used in processing for controlling a content of a display screen displayed on the touch panel monitor 108. This processing is, for example, processing for displaying the image-capturing condition corresponding to the stitch imaging and processing for displaying the generated stitched image on the display screen. Further, by this module, the CPU 401 determines whether any one of the above-described plurality of radiographic imaging units 102a, 102b, and 102c is in the first state or all of the above-described plurality of radiographic imaging units 102a, 102b, and 102c are in the second state based on the information indicating the respective states of the plurality of radiographic imaging units 102a, 102b, and 102c. Then, the CPU 401 controls the display of the touch panel monitor 108 according to this determination. The second NIC 405b receives the state information indicating whether the radiographic imaging unit 102 is in the first state, which is not a state prepared for the acquisition of the radiographic image, or the second state, which is the state prepared for the acquisition of the radiographic image, with respect to each of the plurality of radiographic imaging units 102a, 102b, and 102c. The CPU 401 determines whether any one of the above-described plurality of radiographic imaging units 102a, 102b, and 102c is in the first state or all of the above-described plurality of radiographic imaging units 102a, 102b, and 102c are in the second state.

Controlling the display in this manner allows the control apparatus 104 to present a display indicating whether all of the radiographic imaging units 102a, 102b, and 102c are in the state capable of the image-capturing, instead of a display individually indicating the state of each of the radiographic imaging units 102a, 102b, and 102c, thereby allowing the user to intuitively recognize whether the stitch imaging can be carried out. Alternatively, the control apparatus 104 may also be configured to present the display individually indicating the state of each of the radiographic imaging units 102a, 102b, and 102c, together with the display indicating whether all of the radiographic imaging units 102a, 102b, and 102c are in the state capable of the image-capturing, and it is apparent that such a display allows the user to readily take some measures, for example, when one radiographic imaging unit 102 cannot carry out the image-capturing due to an error.

The image-capturing control module 434 is a program for causing the CPU 401 to integrally control the execution of the radiographic imaging including the stitch imaging. By the image-capturing control module 434, for example, the CPU 401 specifies the image-capturing condition according to the operation input, transmits the signal for requesting the state of each of the units of the radiographic imaging unit 102, and controls the reception of the radiographic images.

The stitched image generation module 435 generates the stitched image from the plurality of radiographic images with use of the CPU 401 and the GPU 406. The stitched image is generated by positioning processing for defining a positional relationship among the plurality of radiographic images. The positioning processing includes rough adjustment processing for determining a rough layout among the images, and fine adjustment processing for adjusting the positions among the images with precision of several pixels, or precision of one pixel or less.

The rough adjustment processing is processing for determining which ends correspond to each other among the ends of the individual radiographic images with use of the information indicating the layout relationship among the plurality of radiographic imaging units 102a, 102b, and 102c. This processing is performed with use of the layout information acquired from the processing performed by the FPD layout acquisition module 431. The fine adjustment processing is performed by, for example, pattern matching processing with use of image information of a region overlapping among the plurality of radiographic images. This processing may be performed after the processing by the correction module 436.

The correction module 436 performs the processing for correcting an influence due to the characteristic of the sensor and the correction processing for reducing the number of structures appearing in the radiographic image(s) with use of the CPU 401 and the GPU 406. The processing for correcting the characteristic of the sensor includes, for example, the processing for correcting influences of the variation in the input/output characteristic of each of the pixels, the defective pixel, and the like, and this processing is performed with use of data such as data for the gain correction and a defective map that are acquired in advance. The correction processing for reducing the number of structures appearing in the radiographic image(s) is performed with use of the correction data for reducing the number of structures. This correction data is acquired by subtracting data acquired by carrying out the image-capturing with use of the same imaging system as the imaging system that captures this radiographic image and without the presence of the subject, after dividing this data by the data for the gain correction or dividing this data thereby after logarithmically converting this data. This correction data may be stored in the radiographic imaging unit 102 in advance at the time of shipment from a factory or the like, or may be acquired before the stitch imaging is carried out in each hospital.

In another exemplary embodiment, the function of the relay 103 is assumed to be provided to the control apparatus 104. In this case, the stitch imaging system is configured in such a manner that, for example, the control apparatus 104 includes three second NICs 405b that communicate with the radiographic imaging units 102a, 102b, and 102c, and cables connected to the radiographic imaging units 102a, 102b, and 102c are directly connected to the control apparatus 104.

The display screen according to the present exemplary embodiment will be described with reference to FIG. 5. A display screen 500 includes an image area 501 where the radiographic image is displayed, a subject area 502 where information about the subject is displayed, a image-capturing information area 503 where the image-capturing information is displayed, an end button 504, and a state area 507 where information indicating the states of the plurality of radiographic imaging units 102a, 102b, and 102c is displayed. The example illustrated in FIG. 5 indicates the display screen after the stitch imaging has been already carried out once when the stitch imaging is supposed to be carried out a plurality of times. A stitched image 508 is displayed in the image area 501. Information about a subject A is displayed in the subject area 502. Image-capturing information 505a about the image-capturing site that is the entire lower limb, and image-capturing information 505b about the image-capturing site that is the entire spine are displayed in the image-capturing information area 503 as image-capturing information 505. The information about the image-capturing site, and the number of radiographic imaging units 102 used or to be used for the stitch imaging thereof are displayed side by side as the image-capturing information 505. The image-capturing information 505a is image-capturing information about the image-capturing that has been already carried out, and thumbnails of the radiographic images from the plurality of radiographic imaging units 102 are displayed therein while being arranged in a layout according to the layout relationship among the radiographic imaging units 102. In the example illustrated in FIG. 5, a thumbnail 506b of the radiographic image from the radiographic imaging unit 102b, a thumbnail 506c of the radiographic image from the radiographic imaging unit 102c, and a thumbnail 506a of the radiographic image from the radiographic imaging unit 102a are displayed while being arranged in this order. In this manner, the thumbnails are arranged based on the layout information, which allows the user to easily check whether the stitch imaging has been appropriately carried out. On the other hand, if there is an error in the layout information, this results in a failure to arrange the thumbnails appropriately, which allows the user to be notified of whether the layout information is appropriate in an easily understandable manner.

On the other hand, the image-capturing information 505b is image-capturing information about the image-capturing that is not yet carried out, and a display indicating the layout relationship among the plurality of radiographic imaging units 102 is presented therein instead of the thumbnails. In the example illustrated in FIG. 5, a display ("FPD B") 507b corresponding to the radiographic imaging unit 102b, a display ("FPD C") 507c corresponding to the radiographic imaging unit 102c, and a display ("FPD A") 507a corresponding to the radiographic imaging unit 102a are displayed while being arranged so as to be located at display positions according to the layout relationship among the radiographic imaging units 102a, 102b, and 102c. This display allows the user to check whether the radiographic imaging units 102a, 102b, and 102c are appropriately laid out on the touch panel monitor 108 of the control apparatus 104 before the image-capturing. The control apparatus 104 may be configured to cause the states of the radiographic imaging units 102a, 102b, and 102c to be displayed by the displays 507a, 507b, and 507c at this time.

The information indicating the states of the plurality of radiographic imaging units 102 is displayed in the state area 507. The radiographic imaging units 102 for which the information indicating the states is displayed there may be the radiographic imaging units 102 corresponding to the currently specified image-capturing condition. If the image-capturing condition corresponding to the stitch imaging is specified as illustrated in FIG. 5, the information indicating the states of the radiographic imaging units 102a, 102b, and 102c is displayed therein. In the state area 507, the pieces of information indicating the states of the plurality of radiographic imaging units 102 are displayed while being arranged on the display screen 500 at display positions according to the layout state among this plurality of radiographic imaging units 102. For example, if the radiographic imaging unit 102b and the radiographic imaging unit 102c are interchanged with the display screen displayed as illustrated in FIG. 5, this interchange results in a display of the respective states of the radiographic imaging units 102c, 102b, and 102a arranged in this order in the state area 507. Presenting the display in this manner allows the user to easily check the layout relationship among the plurality of radiographic imaging units 102.

The end button 504 is a button for ending an examination regarding the plurality of pieces of image-capturing information displayed on the display screen 500. If the end button 504 is pressed after an end of the image-capturing operations corresponding to all pieces of image-capturing information contained in this examination, this examination is ended. In this case, the CPU 401 generates the DICOM image file of the radiographic images regarding this examination, and causes the first NIC 405a to transmit this file to the PACS 153. On the other hand, if the end button 504 is pressed before the end of the image-capturing operations corresponding to the pieces of image-capturing information contained in this examination, this examination is set into a suspended state, and is stored into the storage unit 403 together with flag information indicating the suspended state.

The control apparatus 104 may be configured to cause the states of the individual radiographic imaging units 102 to be displayed in the displays 507a, 507b, and 507c, and cause readiness or unreadiness for the image-capturing to be clearly displayed in the state area 507 as a display indicating whether the stitch imaging can be carried out. In this case, the state area 507 is displayed in such a manner that a color of the state area 507 is, for example, grayed if even any one of the plurality of radiographic imaging units 102 is in the first state, i.e., is not in the state prepared for the acquisition of the radiographic image. Further, for example, a text "NOT READY" is displayed in addition thereto. The prohibition of the stitch imaging is clearly indicated by this display. On the other hand, if all of the plurality of radiographic imaging units 102 are in the second state prepared for the acquisition of the radiographic image, the color of the state area 507 is, for example, greened, and a text "READY" is displayed in addition thereto. The permission of the stitch imaging is clearly indicated by this display. In this manner, the display of the touch panel monitor 108 is controlled according to whether any one of the plurality of radiographic imaging units 102 is in the first state or all of the plurality of radiographic imaging units 102 are in the second state, by which the readiness or the unreadiness for the image-capturing is clearly indicated.

Figure 6:
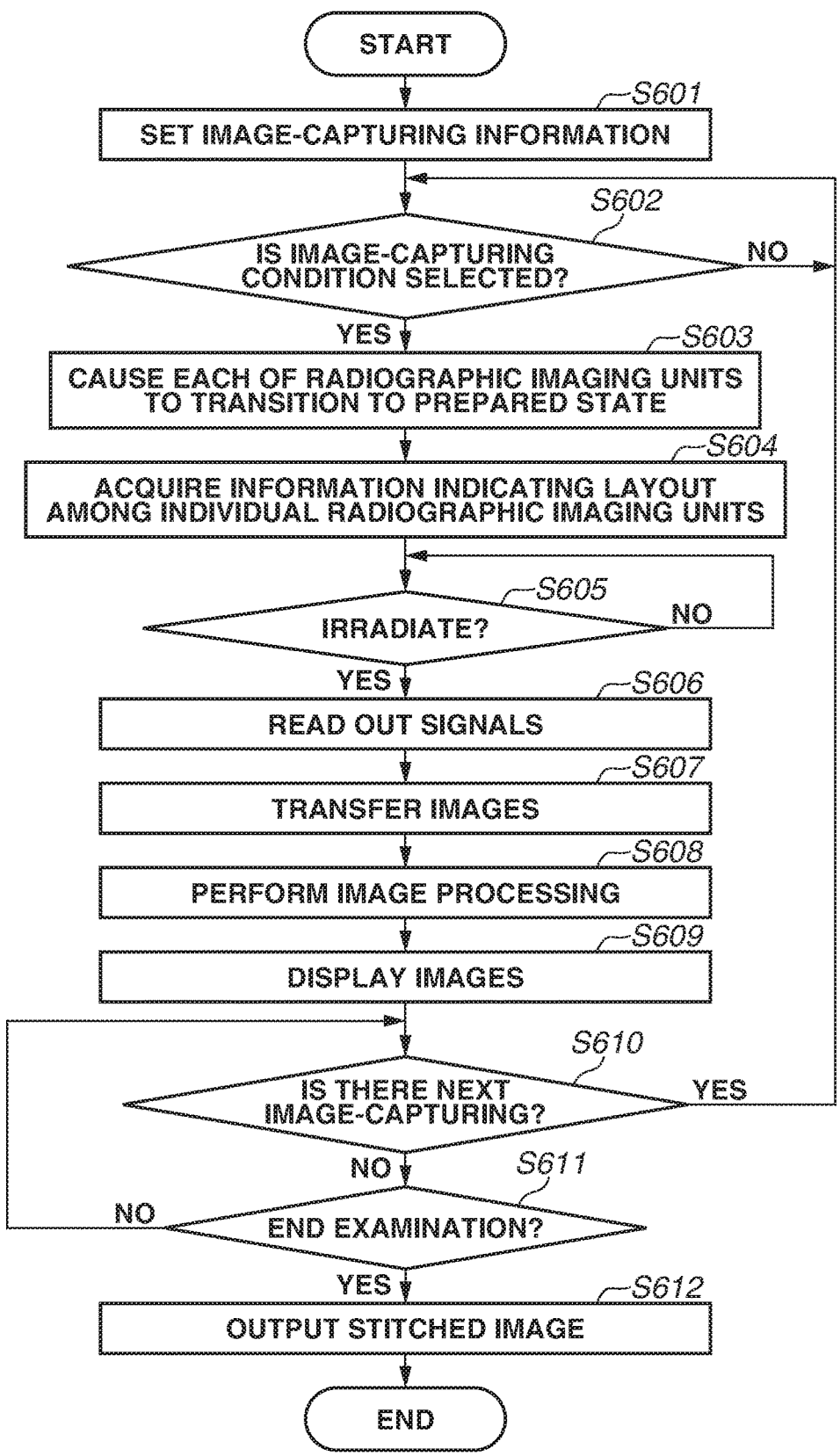
FIG. 6 is a flowchart illustrating a flow of processing regarding stitch imaging according to the exemplary embodiment.

A flow of processing regarding the stitch imaging according to the present exemplary embodiment will be described with reference to a flowchart illustrated in FIG. 6. A processing entity that performs the following processing is the CPU 401 of the control apparatus 104, unless otherwise noted specifically. The flow of the processing from steps S601 to S612 is controlled by the image-capturing control module 434.

In step S601, the CPU 401 sets one of pieces of image-capturing information (pieces of examination information) input from the RIS 151 as an examination target. In this process, for example, according to an operation input by which the user selects one of the plurality of pieces of examination information displayed in the form of a list, the CPU 401 sets this image-capturing information (the examination information) as the image-capturing target. At this time, for example, the CPU 401 executes the display control module 433 to cause the display screen 500 to be displayed on the display unit.

In step S602, the CPU 401 determines whether an operation input for selecting the image-capturing condition corresponding to the stitch imaging that is contained in the image-capturing information (the examination information) is entered. At this time, if the image-capturing information (the examination information) contains a plurality of image-capturing conditions, information corresponding to the plurality of image-capturing conditions is displayed in the image-capturing information area 503 on the display screen 500, and the CPU 401 determines whether an operation input for selecting one of them is entered by the user. If the operation input for the selection is not entered (NO in step S602), the determination process in step S602 is repeated. If the operation input for the selection is entered (YES in step S602), the processing proceeds to a next process. The processing may be configured to automatically proceed to step S603 regardless of the process of step S602, if the image-capturing information (the examination information) contains only the image-capturing condition corresponding to the image-capturing (1).

In step S603, the CPU 401 specifies the image-capturing condition corresponding to the stitch imaging that has been selected by the operation input. Then, according to this specifying, the CPU 401 causes the second NIC 405b to transmit the signals for causing the states to transition to the prepared state to the plurality of radiographic imaging units 102a, 102b, and 102c involved in this stitch imaging. In response thereto, each of the radiographic imaging units 102a, 102b, and 102c apply the bias voltage to the two-dimensional image sensor 120 by the main control circuit 150 controlling the bias power source 140, if the bias voltage is not applied to the two-dimensional image sensor 120. After that, each of the radiographic imaging units 102a, 102b, and 102c carries out the initialization of reading out the image signals from the pixel array by the driving circuit 130 to read out dark current signals stored in the pixels. After an end of the initialization, each of the radiographic imaging units 102a, 102b, and 102c transmits, to the control apparatus 104, the state information indicating that each of the plurality of radiographic imaging units 102a, 102b, and 102c is in the second state, which is the state prepared for the acquisition of the radiographic image, after the completion of the initialization.

In step S604, the CPU 401 acquires the layout information indicating the layout relationship among the plurality of radiographic imaging units 102a, 102b, and 102c to be used for the stitch imaging. For example, in the case where the present processing is performed assuming that the stitch imaging system is a system such as the system illustrated in FIG. 1, the CPU 401 acquires the information indicating the respective communication paths of the plurality of radiographic imaging units 102a, 102b, and 102c from the relay 103. The relay 103 includes a plurality of physical ports to which the cables 205a, 205b, and 205c from the platform connectors 206a, 206b, and 206c respectively provided to the housing portions 201a, 201b, and 201c are connected. This relay 103 identifies which physical port each of the signals from the radiographic imaging units 102a, 102b, and 102c is input from, thereby generating the correspondence relationships between the physical ports and the radiographic imaging units 102a, 102b, and 102c, i.e., the information indicating the respective communication paths of the radiographic imaging units 102a, 102b, and 102c. The CPU 401 of the control apparatus 104 receives this information from the second NIC 405b. The CPU 401 acquires the information indicating the layout relationship from the information indicating the communication paths acquired in this manner.

Figure 5:
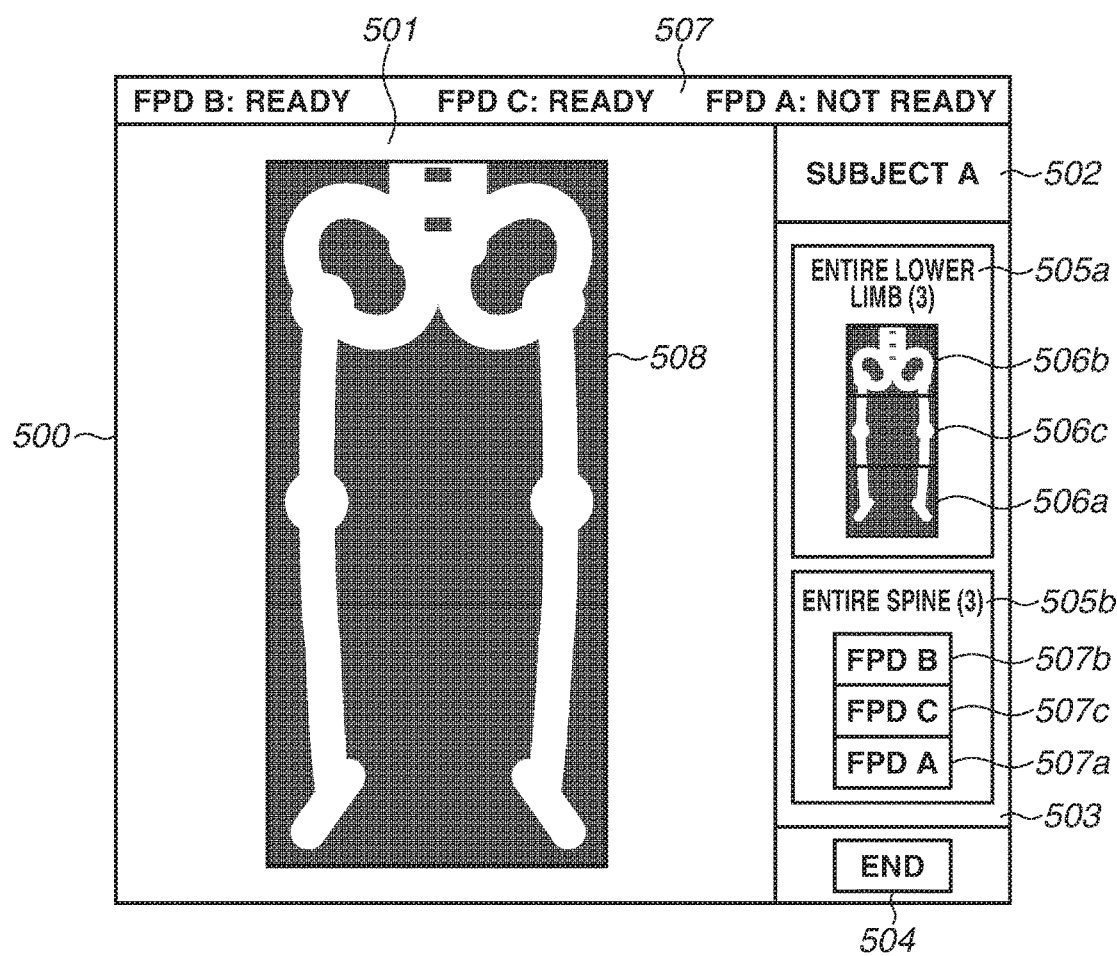
FIG. 5 illustrates an example of a display screen according to the exemplary embodiment.

As indicated by the image-capturing information 505b on the display screen 500 illustrated in FIG. 5, this information indicating the layout relationship is displayed as the information indicating the layout relationship among the plurality of radiographic imaging units 102a, 102b, and 102c to be used for the stitch imaging corresponding to this image-capturing information 505b.

In step S605, the CPU 401 determines whether the irradiation switch is pressed. If the irradiation switch is pressed (YES in step S605), the processing proceeds to step S606.

Whether the irradiation switch should be pressed is determined, for example, with use of the display based on the states of the plurality of radiographic imaging units 102a, 102b, and 102c displayed on the display screen 500. More specifically, the display of the specific area on the display screen 500 is controlled according to whether any one of the plurality of radiographic imaging units 102a, 102b, and 102c is in the first state or all of the plurality of radiographic imaging units 102a, 102b, and 102c are in the second state based on the state information acquired from each of the plurality of radiographic imaging units 102a, 102b, and 102c. This is as described in the description of the display screen 500 illustrated in FIG. 5.

In step S606, the driving circuit 130 of each of the radiographic imaging units 102a, 102b, and 102c reads out the image signals acquired by detecting the radiation with which the subject is irradiated by the readout circuit 170 to generate the digital radiographic image.

In step S607, the wired communication circuit 180 or the wireless communication circuit 160 of each of the radiographic imaging units 102a, 102b, and 102c transmits the generated digital radiographic image to the control apparatus 104. Each of the plurality of radiographic imaging units 102a, 102b, and 102c transmits the preview image small in data quantity and then transmits the image that contains the remaining data after that, thereby completing the transmission of the radiographic image acquired from the image-capturing. At this time, in a case where each of the radiographic imaging units 102a, 102b, and 102c transmits the radiographic image via the wired communication circuit 180, each of the radiographic imaging units 102a, 102b, and 102c employs the communication method that sequentially transmits the preview image and the image containing the remaining data in response to the readout of the image signals. This transmission is carried out asynchronously with the other radiographic imaging units 102. On the other hand, in a case where each of the radiographic imaging units 102a, 102b, and 102c transmits the images via the wireless communication circuit 160, each of the radiographic imaging units 102a, 102b, and 102c restricts the transmission of the image that contains the remaining data until the completion of the transmission of the preview images from all of the radiographic imaging units 102a, 102b, and 102c, in consideration of such a problem that this image transmission may weigh on the communication capacity.

In step S608, the CPU 401 of the control apparatus 104 performs the image processing on the plurality of radiographic images acquired from the plurality of radiographic imaging units 102a, 102b, and 102c with use of the GPU 406 and the like. This processing is, for example, the processing for generating the stitched image with use of the stitched image generation module 435, and the processing for reducing the number of structure images with use of the correction module 436. In the process of step S608, first, the CPU 401 performs the processing for acquiring a preview stitched image from the plurality of preview images, and then performs the processing for acquiring the stitched image from the plurality of radiographic images larger in data amount than these preview images after that. This processing is performed with use of the layout information acquired in step S604. The processing for reducing the number of structure images is performed on the radiographic image specified based on the layout information with use of the correction data prepared for the processing for reducing the number of structure images that is specified based on the layout information.

In step S609, the CPU 401 causes the preview stitched image and the stitched image acquired from the processing performed by the GPU 406 and the like to be displayed on the display unit.

In step S610, the CPU 401 determines whether there is an image-capturing condition on which the image-capturing is not yet carried out. If there is such an image-capturing condition (YES in step S610), the processing proceeds to step S602. Then, the CPU 401 performs the stitch imaging based on the new image-capturing condition. If there is no image-capturing condition on which the image-capturing is not yet carried out (NO in step S610), then in step S611, the CPU 401 determines whether to end the examination. If the CPU 401 does not end the examination (NO in step S611), the CPU 401 performs processing for waiting for an addition of an image-capturing condition on which the image-capturing is not yet carried out, or an instruction to end the examination. If the examination end button 504 is pressed at this time (YES in step S611), the CPU 401 ends the examination. In step S612, the CPU 401 causes the first NIC 405a to output the DICOM image file of the stitched image to the PACS 153. With this output, the examination that contains the stitch imaging is ended.

In the above-described example, the stitch imaging system is assumed to carry out the stitch imaging a plurality of times during a single examination. However, it is not limited thereto, and it may be assumed to carry out the stitch imaging together with image-capturing using a different image-capturing method from the stitch imaging during a single examination. In this manner, in the case of the imaging system capable of carrying out the stitch imaging, when carrying out the stitch imaging, the control apparatus 104 transmits the signals for causing the states of the plurality of radiographic imaging units 102a, 102b, and 102c to transition according to the specifying of the image-capturing condition. On the other hand, when carrying out the image-capturing using the single radiographic imaging unit 102, such as normal image-capturing, the control apparatus 104 transmits the signal for causing the state of this single radiographic imaging unit 102 to transition according to the specifying of the image-capturing condition. Further, when carrying out the stitch imaging, the control apparatus 104 controls the display based on the state information acquired from each of the plurality of radiographic imaging units 102a, 102b, and 102c according to whether any one of the plurality of radiographic imaging units 102a, 102b, and 102c is in the first state or all of the plurality of radiographic imaging units 102a, 102b, and 102c are in the second state. When carrying out the image-capturing using the single radiographic imaging unit 102, the control apparatus 104 causes the information indicating the state of this single radiographic imaging unit 102 to be displayed.

Further, when carrying out the stitch imaging, the control apparatus 104 acquires the layout information indicating the layout relationship among the plurality of radiographic imaging units 102a, 102b, and 102c. The radiographic image(s) acquired from at least one of the radiographic imaging unit(s) 102 specified based on this layout information is or are corrected based on the correction data specified based on the layout information.

Further, at the time executing the stitch imaging, the control is performed so as to restrict the transmission of the image according to the communication of the other radiographic imaging units 102 in consideration of the problem that the image transmission may weigh on the communication capacity. On the other hand, at the time of the image-capturing using the single radiographic imaging unit 102, the image that contains the remaining data is transmitted according to the end of the transmission of the preview image because priority is placed on transmitting the image as quickly as possible in this case.

Figure 7:
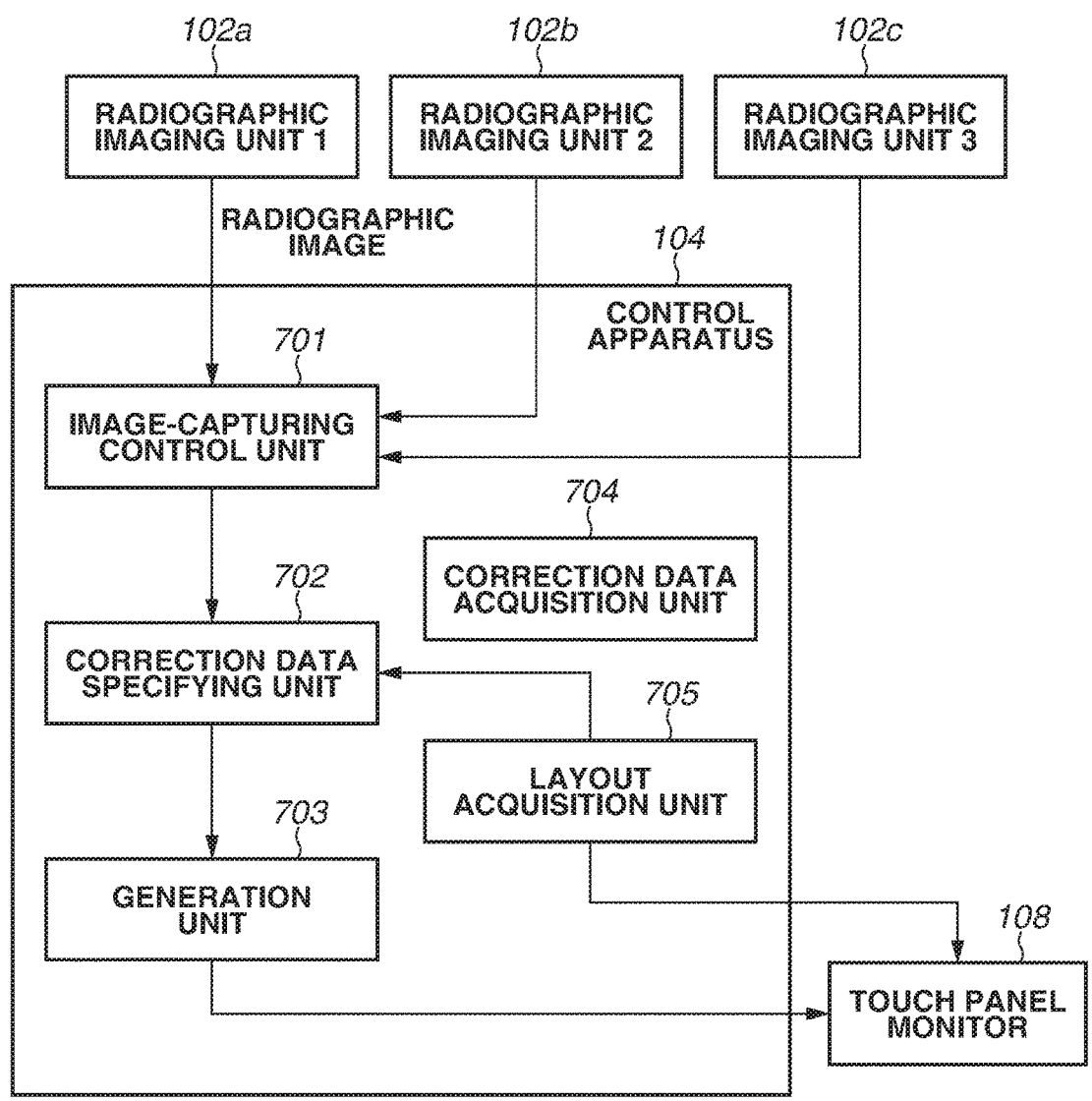
FIG. 7 is a block diagram illustrating functions of the control apparatus according to the exemplary embodiment.

The functions included in the control apparatus 104 according to one exemplary embodiment of the present invention will be described with reference to FIG. 7. The control apparatus 104 includes an image-capturing control unit 701, a correction data specifying unit 702, a generation unit 703, a correction data acquisition unit 704, and a layout acquisition unit 705. Each of these units may be implemented by a hardware circuit, or may be realized by collaboration between a software program and hardware as illustrated in FIG. 4. In a case where each of the units is realized with use of the software program, the image-capturing control unit 701, the correction data specifying unit 702, the generation unit 703, and the layout acquisition unit 705 correspond to the image-capturing control module 434, the correction module 436, the stitched image generation module 435, and the FPD layout acquisition module 431, respectively. The correction data acquisition unit 704 will be described below in detail in terms of an operation thereof with reference to FIG. 10. The correction data specifying unit 702 corresponds to the function of specifying the correction data to be used for the correction of the structure.

In a case where each of the above-described units is implemented by the hardware circuit, converting each of these software modules into information indicating a configuration of an FPGA allows them to be realized by the FPGA.

Figure 8:
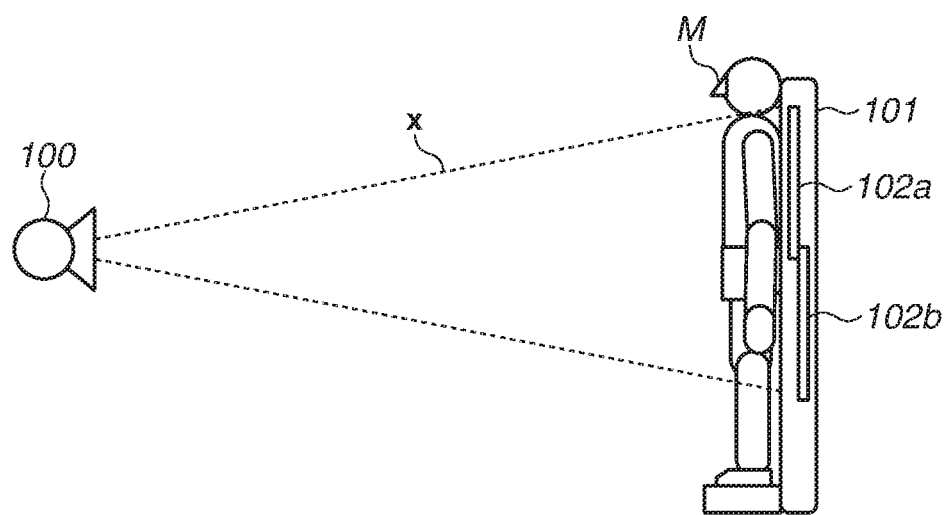
FIG. 8 illustrates an example of the stitch imaging system according to the exemplary embodiment.

Examples of the layout state between or among the radiographic imaging units 102 to be used for the stitch imaging will be described with reference to FIGS. 8 and 9. The example illustrated in FIG. 8 is an example in which the stitch imaging is carried out with use of two radiographic imaging units 102. This example corresponds to, for example, such a state that the radiographic imaging units 102a and 102b are housed in the housing portions 201a and 201b of the platform 101 illustrated in FIG. 1, respectively, but no radiographic imaging unit 102 is housed in the housing portion 201c. In this case, a structure of a lower end of the radiographic imaging unit 102a appears at an upper end of the radiographic image from the radiographic imaging unit 102b, but no structure appears at a lower end of the radiographic image from the radiographic imaging unit 102b, unlike the example illustrated in FIG. 1. Then, the radiation emitted from the radiation generation unit 100 for the irradiation reaches a detection region defined by the radiographic imaging units 102a and 102b. A focal point of the radiation generation unit 100 is placed on a line that is normal to the detection region while extending from a substantially central position of the radiographic imaging units 102a and 102b.

Figure 9:
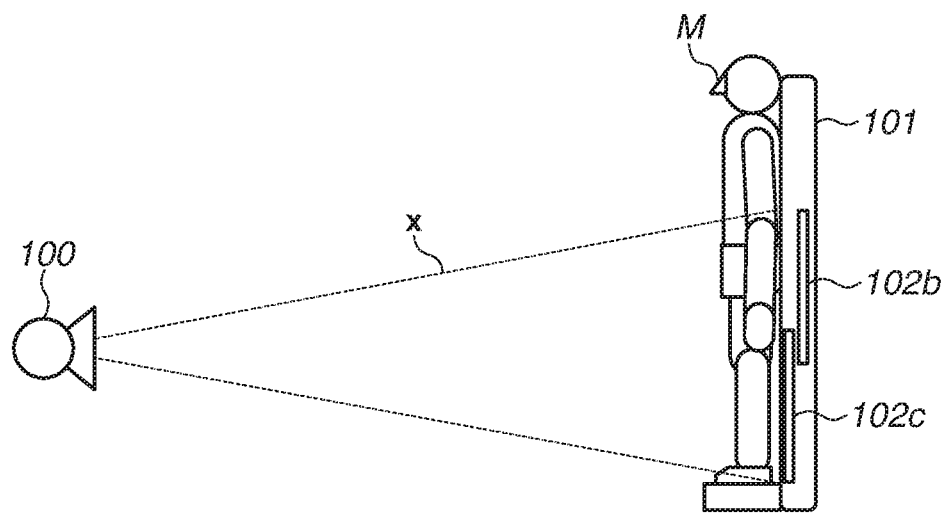
FIG. 9 illustrates another example of the stitch imaging system according to the exemplary embodiment.

The example illustrated in FIG. 9 is an example in which the stitch imaging is carried out with use of two radiographic imaging units 102, similarly to FIG. 8. This example corresponds to, for example, such a state that the radiographic imaging units 102b and 102c are housed in the housing portions 201b and 201c of the platform 101 illustrated in FIG. 1, respectively, but no radiographic imaging unit 102 is housed in the housing portion 201a. In this case, a structure of an upper end of the radiographic imaging unit 102c appears at the lower end of the radiographic image from the radiographic imaging unit 102b but no structure appears at the upper end of the radiographic image from the radiographic imaging unit 102b, unlike the example illustrated in FIG. 1. Then, the radiation emitted from the radiation generation unit 100 for the irradiation reaches a detection region defined by the radiographic imaging units 102b and 102c. The focal point of the radiation generation unit 100 is placed on a line that is normal to the detection region while extending from a substantially central position of the radiographic imaging units 102b and 102c.

In comparison with these examples illustrated in FIGS. 8 and 9, the example illustrated in FIG. 1 is an example in which the stitch imaging is carried out with use of three radiographic imaging units 102. The radiographic imaging units 102a, 102b, and 102c are housed in the housing portion 201a, 201b, and 201c of the platform 101, respectively. In this case, the structure of the lower end of the radiographic imaging unit 102a appears at the upper end of the radiographic image from the radiographic imaging unit 102b, and the structure of the upper end of the radiographic imaging unit 102c appears at the lower end of the radiographic image from the radiographic imaging unit 102b. Then, the radiation emitted from the radiation generation unit 100 for the irradiation reaches a detection region defined by the radiographic imaging units 102a, 102b, and 102c. The focal point of the radiation generation unit 100 is placed on a line that is normal to the detection region while extending from around a substantially central position of the radiographic imaging units 102a, 102b, and 102c. In other words, the focal point of the radiation generation unit 100 is placed on a line that is normal to the detection region while extending from a substantially central position of the radiographic imaging unit 102b.

Among these examples illustrated in FIGS. 1, 8, and 9, the radiographic imaging units 102 and the focal point of the radiation generation unit 100 are arranged in a different layout relationship from one another, which results in the appearance of a different structure image from one another in the radiographic image acquired from the radiographic imaging unit 102b. In this manner, since how the structure image appears varies depending on the layout relationship of the imaging system, the correction data for reducing the number of structure images is held for each layout of the imaging system.

In one exemplary embodiment, the difference in the layout relationship of the imaging system may be able to be dealt with by, for example, deforming the structure image if this difference is not so large, whereby the correction data does not necessarily have to be held for each layout of the imaging system.

Figure 10:
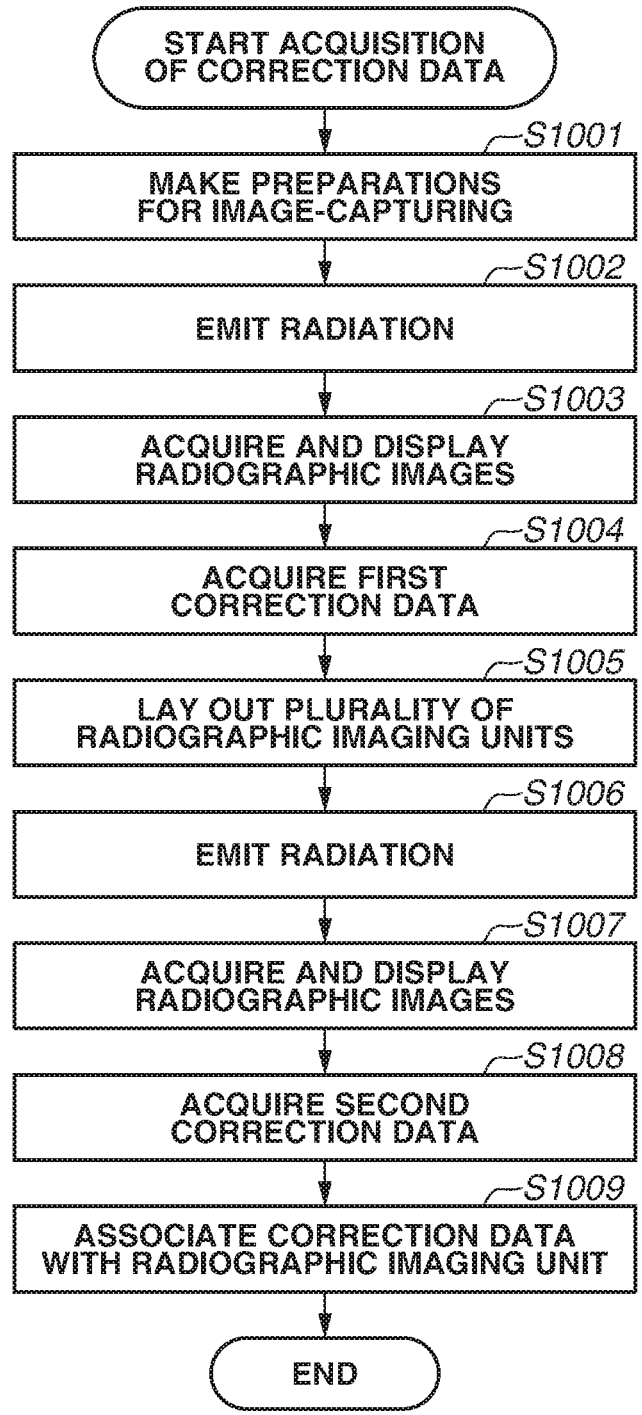
FIG. 10 is a flowchart illustrating a flow of processing for acquiring correction data according to the exemplary embodiment.

A flow of processing for acquiring the correction data for reducing the number of structure images will be described with reference to a flowchart illustrated in FIG. 10. This processing is performed for each of the radiographic imaging units 102a, 102b, and 102c.

In step S1001, the image-capturing control unit 701 makes preparations for the image-capturing. In this process, the image-capturing control unit 701 causes the second NIC 405b to transmit the signal containing the instruction for instructing each of the radiographic imaging units 102a, 102b, and 102c to transition to the state prepared for the radiography to each of the plurality of radiographic imaging units 102a, 102b, and 102c.

In step S1002, the radiation generation unit 100 emits the radiation according to pressing of the irradiation switch, and the plurality of radiographic imaging units 102a, 102b, and 102c detects the radiation and acquires the radiographic image signals. At this time, the radiographic images are acquired by emission of substantially uniform radiation to the radiographic imaging units 102a, 102b, and 102c with these radiographic imaging units 102a, 102b, and 102c laid out in such a manner that the predetermined structure does not appear in the radiographic images from the radiographic imaging units 102a, 102b, and 102c. The images acquired at this time are so-called white images.

In step S1003, the control apparatus 104 acquires the radiographic images from the plurality of radiographic imaging units 102a, 102b, and 102c, and for example, causes these images to be displayed on the touch panel monitor 108.

In step S1004, the correction data acquisition unit 704 acquires gain data, which is first correction data indicating the variation in the input/output characteristic of each of the pixels of the radiation sensor 110, from these white images by performing processing such as calculating a reciprocal.

In step S1005, the other radiographic imaging units 102 are arranged so as to be located according to a predetermined positional relationship relative to the radiographic imaging unit 102 with respect to which this correction data is acquired. In the present example, the radiographic imaging units 102 are arranged in such a manner that, between one radiographic imaging unit 102 with respect to which this correction data is acquired and the radiation generation unit 100 that emits the radiation to this one radiographic imaging unit 102, one or a plurality of radiographic imaging unit(s) 102 partially overlap(s) this one radiographic imaging unit 102. More specifically, the imaging system is constructed according to the layout relationship illustrated in any of FIGS. 1, 8, and 9, i.e., the layout relationship when the stitch imaging is carried out.

In step S1006, the radiation generation unit 100 emits the radiation without the subject placed between the radiation generation unit 100 and the radiographic imaging units 102a, 102b, and 102c in the imaging system constructed according to the above-described layout relationship.

In step S1007, the control apparatus 104 acquires the radiographic images from the plurality of radiographic imaging units 102a, 102b, and 102c, and for example, causes these images to be displayed on the touch panel monitor 108.

In step S1008, the correction data acquisition unit 704 acquires structure data for reducing the number of structure images from the radiographic image, which is second correction data, from the plurality of images acquired in step S1007 and the gain data. In this process, the correction data acquisition unit 704 acquires other gain data indicating the variation in the input/output characteristic of each of the pixels of the radiation sensor 110 from the plurality of radiographic images acquired in step S1007 by performing processing such as calculating a reciprocal. However, this other gain data is acquired with an image based on the structure image appearing therein. Therefore, a portion corresponding to the structure image can be extracted by dividing the other gain data by the gain data acquired in step S1004. In this manner, the correction data for reducing the number of structure images is acquired.

In step S1009, the control apparatus 104 associates these first correction data and second correction data with the current target radiographic imaging unit 102. For example, the control apparatus 104 adds the identification information of this radiographic imaging unit 102 to each of files of the first correction data and the second correction data as appendant information. Alternatively, the control apparatus 104 is assumed to cause the radiographic imaging unit 102 to store these first correction data and second correction data therein.

The first correction data and the second correction data will be used for the gain correction of the radiographic image and the processing for reducing the number of structure images, respectively.

The processing from steps S1005 to S1008 is performed for each of layouts of the imaging system that are possible or expected to be employed, such as the examples illustrated in FIGS. 1, 8, and 9.

Laying out the radiographic imaging units 102a, 102b, and 102c as illustrated in FIGS. 1, 8, and 9 requires the acquisition of the structure data for each of them, and the correction of the overlap portion when the combined image is generated. The acquisition of the structure data itself is similar to the normal image-capturing as indicated by steps S1001 to 1004, but this processing includes execution of step S1009 of associating the correction data with the state in which the image-capturing has been carried out among the states illustrated in FIGS. 1, 8, and 9.

Figure 11:
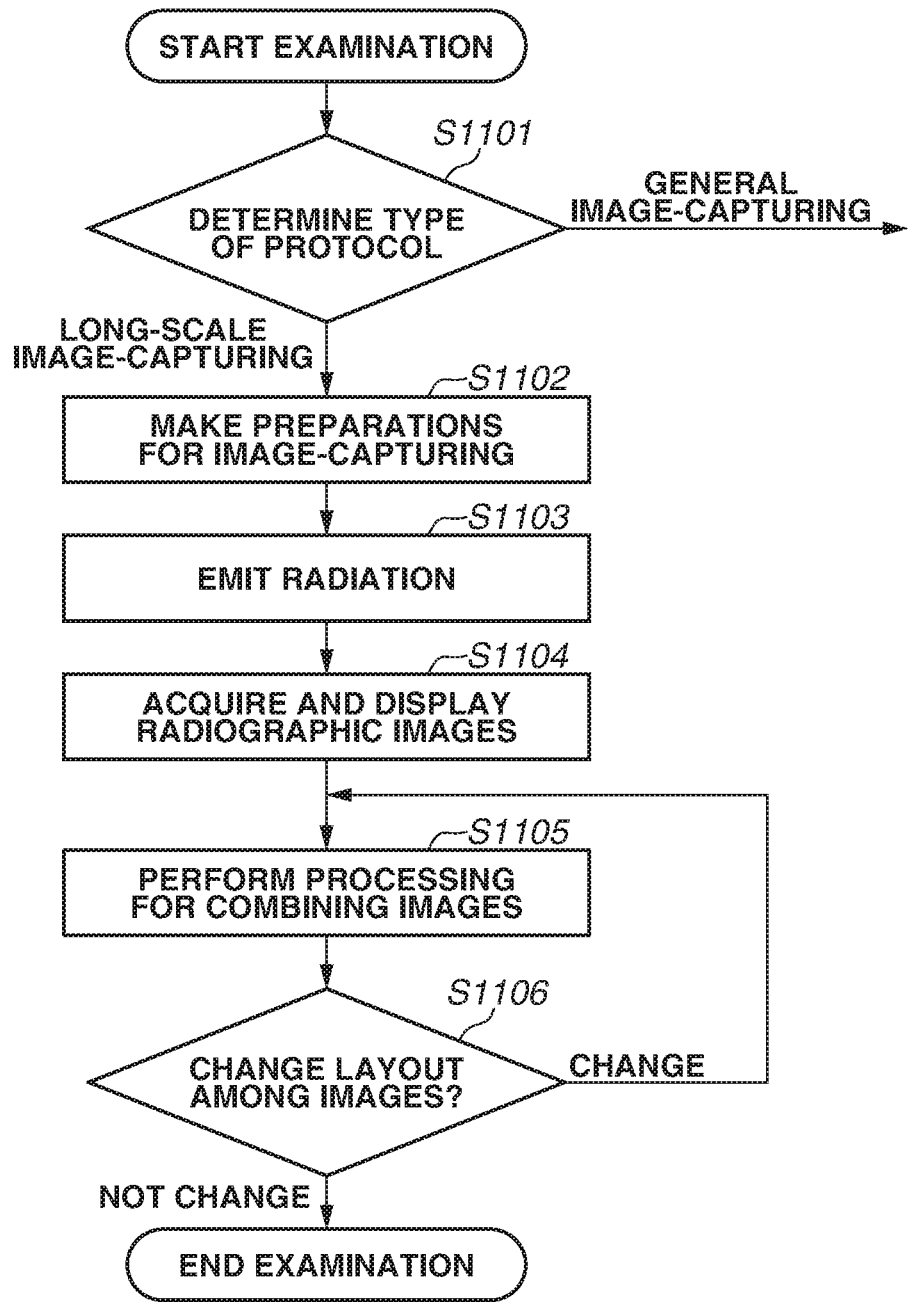
FIG. 11 is a flowchart illustrating a flow of the stitch imaging according to the exemplary embodiment.

A flow of the stitch imaging will be described with reference to a flowchart illustrated in FIG. 11. In step S1101, the control apparatus 104 determines whether a selected protocol is the stitch imaging. If the selected protocol is the stitch imaging (STITCH IMAGING in step S1101), in step S1102, the control apparatus 104 controls the sensors to be used for the image-capturing to transition to the state capable of the image-capturing. Subsequent steps S1103 and S1104 are similar to those of the normal image-capturing. In step S1105, the correction data specifying unit 702 acquires information indicating the number of images captured by the stitch imaging from the protocol in advance, and selects the structure data acquired in any of the states illustrated in FIGS. 1, 8, and 9. In step S1105, the generation unit 703 corrects the image of the portion where the overlap portion appears with use of the acquired structure data to generate the stitched image.

Figure 12:
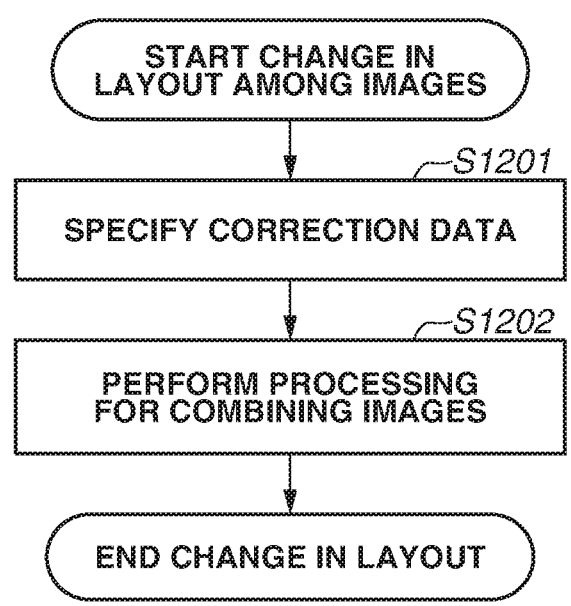
FIG. 12 is a flowchart illustrating a flow of processing for changing a layout state among images.
Figure 14:
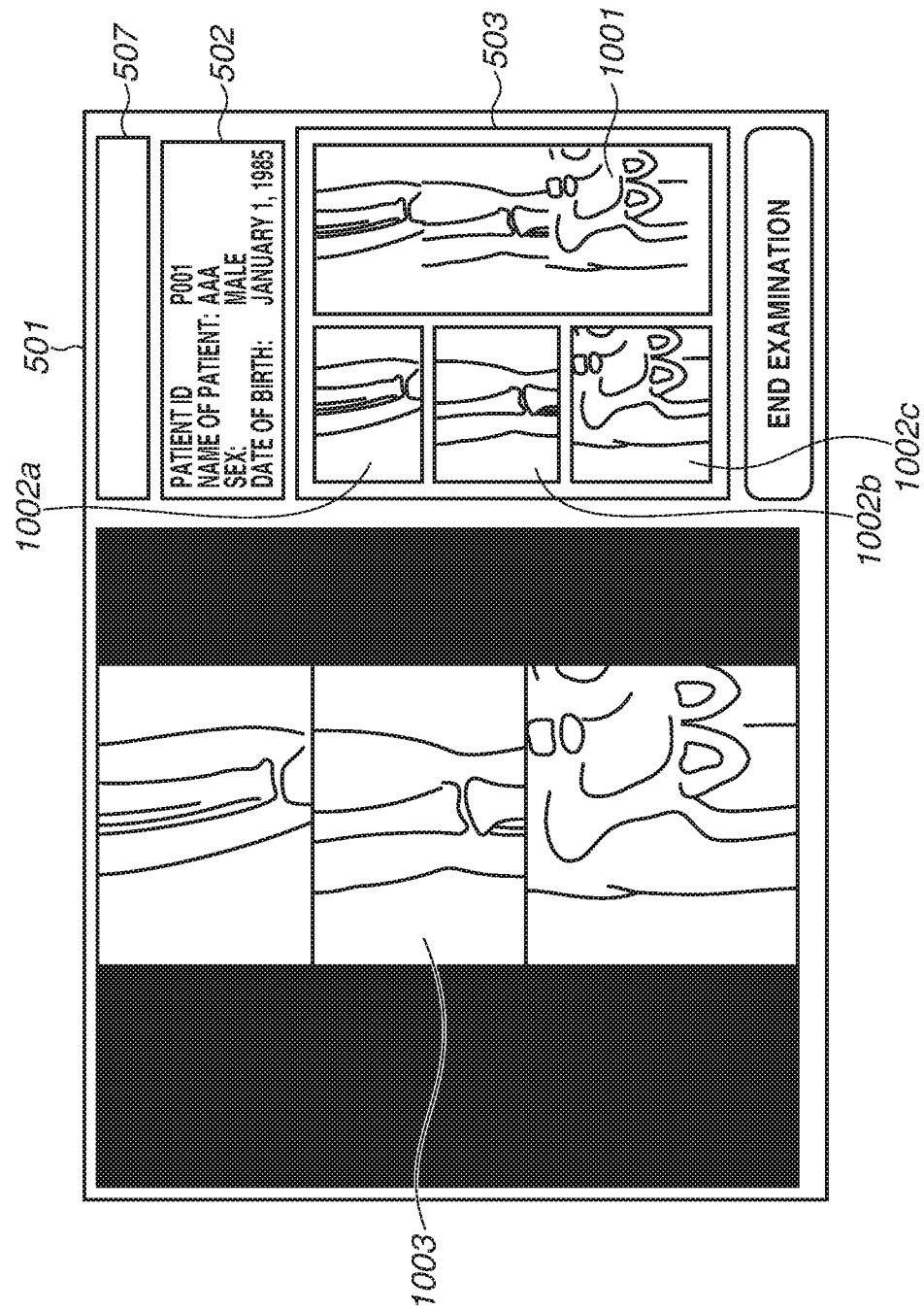
FIG. 14 illustrates an example of the display screen according to the exemplary embodiment.

Another exemplary embodiment of the present invention will be described with reference to FIGS. 12 and 14. FIG. 12 is a flowchart illustrating a flow of processing for changing the layout among the images. FIG. 14 illustrates an example of the display screen 500 displayed on the touch panel monitor 108. In the present exemplary embodiment, the control apparatus 104 may be assumed to change the layout information by acquiring the layout information again based on an operation performed by the user after the image-capturing. This is useful, for example, when there is a mistake in the layout positions of the radiographic imaging units 102a, 102b, and 102c disposed at the long-scale platform 101 or the selection of the protocol with which the image-capturing is carried out.

In this case, an image combined according to an incorrect layout is displayed in a long-scale thumbnail area 1001. The same applies to a display of a stitched image 1003. The user determines an arrangement order by dragging and dropping the radiographic image displayed in a reduced manner in any of thumbnail areas 1002a, 1002b, and 1002c to an arbitrary position. This operation interchanges the position of the radiographic image corresponding to the thumbnail area located at a start point from which the drag operation moves, and the position of the radiographic image corresponding to the thumbnail area located at a destination to which the drag operation moves. This processing results in a change in the layout information acquired by the layout acquisition unit 705 according thereto.

According to this change, in step S1201, the control apparatus 104 performs processing for correcting the structure data with use of the structure data according to the number of images captured by the radiographic imaging units 102. Then, in step S1202, the control apparatus 104 generates the combined image.

Figure 13:
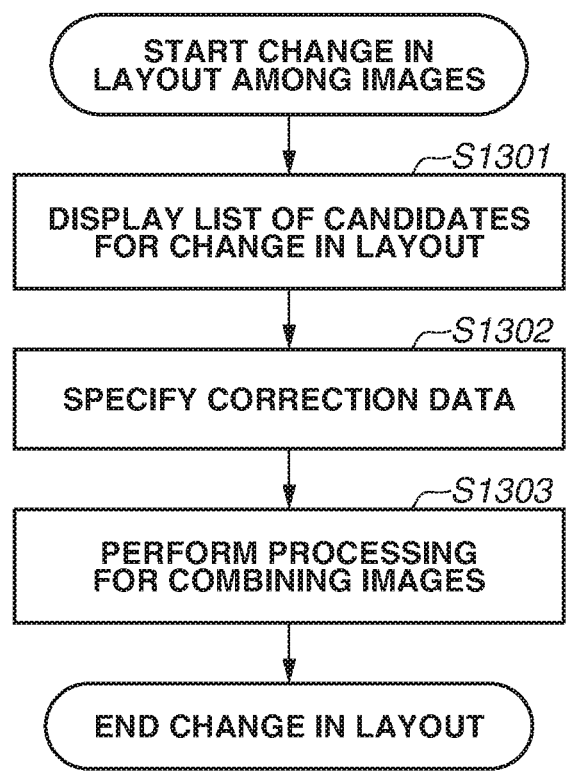
FIG. 13 is a flowchart illustrating a flow of processing for changing the layout state among the images.
Figure 15:
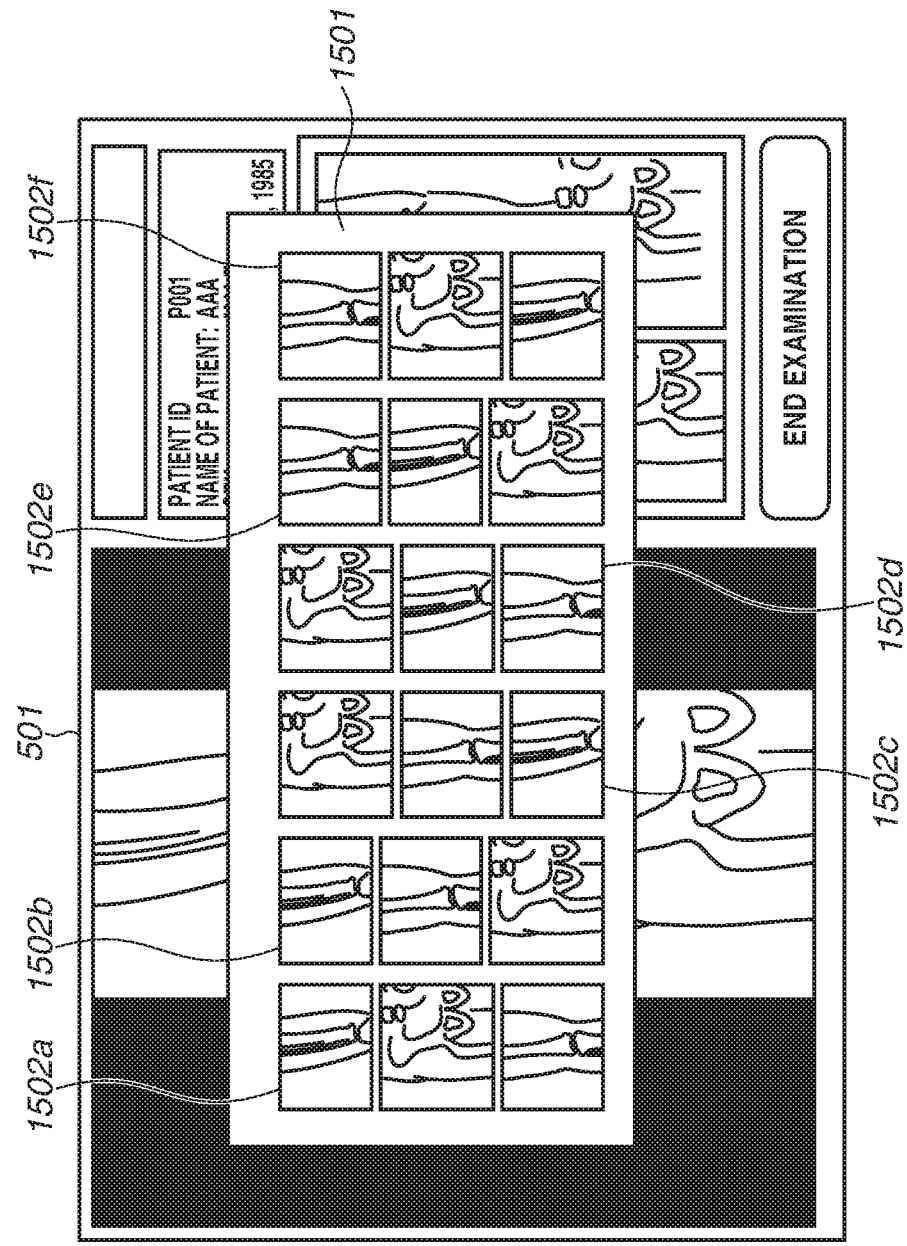
FIG. 15 illustrates another example of the display screen according to the exemplary embodiment.

The layout acquisition unit 705 and processing thereby according to another exemplary embodiment will be described with reference to FIGS. 13 and 15. FIG. 13 is a flowchart illustrating a flow of processing for changing the layout among the images. FIG. 15 illustrates an example of the display screen of image area 501 displayed on the touch panel monitor 108. In step S1301, the CPU 401 of the control apparatus 104 may cause a list display 1501, which contains information indicating candidates for the rearrangement, to be displayed, and may allow the user to select the rearrangement among them.

At this time, a plurality of candidates of the layout state among the radiographic images is displayed in the list display 1501. In the example illustrated in FIG. 15, six candidates, candidates 1501a, 1501b, 1501c, 1501d, 1501e, and 1501f are displayed. As for each of the candidates 1501a to 1501f, the thumbnails of the radiographic images from the radiographic imaging units 102a, 102b, and 102c are arranged in a layout according to the layout state regarding this candidate. Displaying these candidates 1501a to 1501f allows the user to further easily understand the layout state from the thumbnails. It is considered that inappropriateness of the layout state, if any, is often considerably obvious to the user such as a technician, so that this display makes it easier to change the layout state. Further, this display allows the user to change the layout state with just one click, i.e., one operation, without having to perform the drag and drop operation as illustrated in FIG. 14, thereby contributing to promoting efficiency of the operation input. Especially in a case where the touch panel monitor 108 is used, since the click operation is significantly easier to perform than an operation such as the drag and drop operation, this display is also convenient from this point of view. This configuration results in a change from the layout regarding the layout information acquired by the layout acquisition unit 705 to the layout corresponding to the candidate regarding the selection according to the user's entering the above-described operation input of selecting any of the candidates 1501a to 1501f.

As described above, the user's selecting the layout among the images is followed by the subsequent steps. In step S1302, the control apparatus 104 selects the structure data corresponding to the number of images captured by the radiographic imaging units 102, and performs the processing for correcting the structure data. Then, the control apparatus 104 generates the combined image.

In the above-described exemplary embodiments, the radiographic imaging units 102a, 102b, and 102c are each assumed to transmit the preview image smaller in data amount than the radiographic image acquired from the image-capturing, and then transmit the image that contains the remaining data (the entire image or the second to fourth reduced images) after that, but are not limited thereto. For example, the radiographic imaging units 102a, 102b, and 102c may be each configured to transmit the radiographic image without generating the preview image.

The control apparatus 104 in the above-described exemplary embodiments is a single apparatus. However, in another exemplary embodiment, the functions of this image-capturing control apparatus 104 are realized by a control system including a plurality of information processing apparatuses. In this case, the plurality of information processing apparatuses each includes a communication circuit, and is communicable with one another by this communication circuit. One of the plurality of information processing apparatuses can be configured to function as an image processing unit that generates the stitched image, and another apparatus can be configured to function as a control unit. This plurality of information processing apparatuses only has to be communicable at a predetermined communication rate, and does not have to be set up in a same hospital facility or a same country. Further, this control system can also be configured to use, for example, a server apparatus or a server group shared among a plurality of control systems as the image processing unit.

Further, exemplary embodiments of the present invention also include an exemplary embodiment in which a program of software capable of realizing the functions of the above-described exemplary embodiments is supplied to a system or an apparatus, and a computer of this system or apparatus reads out and executes a code of this supplied program.

Therefore, the program code itself installed in this computer for realizing the processing according to the exemplary embodiments by the computer is also one exemplary embodiment of the present invention. Further, an operating system (OS) or the like running on the computer partially or entirely performs the actual processing based on an instruction contained in the program read out by the computer, and the functions of the above-described exemplary embodiments can also be realized by this processing.

An exemplary embodiment constructed by arbitrarily combining the above-described exemplary embodiments is also included in exemplary embodiments of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-017884, filed Jan. 30, 2015, which is hereby incorporated by reference herein in its entirety.

What is claimed is:

1. An imaging system comprising:
a memory storing a program; and
one or more processors which, by executing the program, operate to:
   acquire correction data generated based on first image data including a structure in a first radiographic imaging unit of a plurality of radiographic imaging units, wherein the first image data is generated based on radiation that passes through the first radiographic imaging unit;
   obtain second image data generated based on radiation received after the correction data has been acquired; and
   correct the second image data based on the correction data.

2. The imaging system according to claim 1, wherein the one or more processors further operate to acquire the first image data from a second radiographic imaging unit of the plurality of radiographic imaging units by emitting radiation to the first radiographic imaging unit while the first radiographic imaging unit partially overlapped the second radiographic imaging unit.

3. The imaging system according to claim 2, wherein the one or more processors further operate to correct the second image data based on information corresponding to a layout relationship among a plurality of radiographic imaging units.

4. The imaging system according to claim 3, further comprising a radiation generation unit configured to emit radiation.

5. The imaging system according to claim 1, further comprising a plurality of radiographic imaging units and a plurality of housing portions that house the plurality of radiographic imaging units,
wherein the one or more processors further operate to obtain the second image data from one radiographic imaging unit among the plurality of radiographic imaging units that is housed in a specific housing portion among the plurality of housing portions.

6. The imaging system according to claim 5, further comprising a radiation generation unit configured to emit radiation,
wherein the plurality of radiographic imaging units comprise a second radiographic imaging unit and a third radiographic imaging unit,
wherein the plurality of housing portions house the first radiographic imaging unit, the second radiographic imaging unit, and the third radiographic imaging unit in such a manner that the first radiographic imaging unit, the second radiographic imaging unit, and the third radiographic imaging unit are arranged in this order, respectively, and
wherein the first radiographic imaging unit, the second radiographic imaging unit, and the third radiographic imaging unit are arranged in such a manner that the first radiographic imaging unit and the third radiographic imaging unit partially overlap the second radiographic imaging unit.

7. The imaging system according to claim 1, wherein the first image data is generated based on radiation that does not pass through a subject to be examined.

8. The imaging system according to claim 1, wherein the second image data includes the structure in the first radiographic imaging unit.

9. The imaging system according to claim 8, wherein the one or more processors further operate to obtain the second image data generated based on radiation that is passed through a subject to be examined.

10. The imaging system according to claim 1, wherein the first image data is generated based on radiography in which radiation is emitted to a second radiographic imaging unit of the plurality of radiographic imaging units without a subject to be examined.

11. The imaging system according to claim 1, wherein the one or more processors further operate to acquire the correction data by comparing at least the first image data and another image data.

12. An imaging system comprising:
a memory storing a program; and
one or more processors which, by executing the program, operate to:
   acquire correction data generated based on first image data including a structure in a first radiographic imaging unit, wherein the first image data is generated based on radiation that passes through the first radiographic imaging unit;
   obtain second image data including the structure in the first radiographic imaging unit, wherein the second image data is generated based on radiation that passes through the first radiographic imaging unit and a subject to be examined; and
   correct the second image data based on the correction data.

13. A radiographing apparatus, comprising:
a plurality of radiographic imaging units including a first radiographic imaging unit, each configured to acquire a radiographic image by detecting radiation;
a memory storing a program; and
one or more processors which, by executing the program, operate to:

acquire correction data generated based on first image data including a structure in the first radiographic imaging unit, wherein the first image data is generated based on radiation that passes through the first radiographic imaging unit;

obtain second image data generated based on radiation received after the correction data has been acquired; and correct the second image data based on the correction data.

14. A method for controlling imaging, the method comprising:

acquiring correction data generated based on first image data including a structure in a first radiographic imaging unit, wherein the first image data is generated based on radiation that passes through the first radiographic imaging unit;

obtaining second image data generated based on radiation received after the correction data has been acquired; and correcting the second image data based on the correction data.

15. The method according to claim 14, wherein the first image data is generated based on radiation that does not pass through a subject to be examined.

16. The method according to claim 14, wherein the second image data includes the structure in the first radiographic imaging unit.

17. The method according to claim 16, wherein the obtaining second image data comprises obtaining the second image data generated based on radiation that is passed through a subject to be examined.

18. The method according to claim 14, wherein the first image data is generated based on radiography in which radiation is emitted to a second radiographic imaging unit without a subject to be examined.

19. The method according to claim 14, wherein the acquiring correction data comprises acquiring the correction data generated by comparing at least the first image data and another image data.

20. A non-transitory computer-readable storage medium storing a program for causing a computer to perform operations comprising:

acquiring correction data generated based on first image data including a structure in a first radiographic imaging unit, wherein the first image data is generated based on radiation that passes through the first radiographic imaging unit;

obtaining second image data generated based on radiation received after the correction data has been acquired; and correcting the second image data based on the correction data.

* * * * *